(12) United States Patent
Melozzi

(10) Patent No.: US 11,331,193 B2
(45) Date of Patent: May 17, 2022

(54) HIP PROSTHESIS HEAD

(71) Applicant: Alessandro Melozzi, Teramo (IT)

(72) Inventor: Alessandro Melozzi, Teramo (IT)

( * ) Notice: Subject to any disclaimer, the term of this patent is extended or adjusted under 35 U.S.C. 154(b) by 5 days.

(21) Appl. No.: 16/984,682

(22) Filed: Aug. 4, 2020

(65) Prior Publication Data

US 2021/0045883 A1 Feb. 18, 2021

(30) Foreign Application Priority Data

Aug. 13, 2019 (IT) .................... 102019000014742

(51) Int. Cl.
*A61F 2/36* (2006.01)
*A61F 2/30* (2006.01)

(52) U.S. Cl.
CPC .. *A61F 2/3609* (2013.01); *A61F 2002/30153* (2013.01); *A61F 2002/30158* (2013.01); *A61F 2002/30205* (2013.01); *A61F 2002/30224* (2013.01); *A61F 2002/365* (2013.01); *A61F 2002/3621* (2013.01); *A61F 2002/3631* (2013.01)

(58) Field of Classification Search
CPC .................. A61F 2/3609; A61F 2/4014; A61F 2002/3631; A61F 2002/365; A61F 2002/4033; A61F 2002/4037
See application file for complete search history.

(56) References Cited

U.S. PATENT DOCUMENTS

| | | | | |
|---|---|---|---|---|
| 5,037,441 A * | 8/1991 | Bouvet | ........... | A61F 2/3609 623/22.43 |
| 5,156,624 A * | 10/1992 | Barnes | ........... | A61F 2/3609 623/22.45 |
| 6,059,830 A * | 5/2000 | Lippincott, III | ........... | A61F 2/32 623/18.11 |
| 8,246,687 B2 * | 8/2012 | Katrana | ........... | A61F 2/4014 623/19.13 |
| 8,663,327 B2 * | 3/2014 | Kumar | ........... | A61F 2/3609 623/16.11 |
| 2006/0188845 A1 * | 8/2006 | Serafin, Jr. | ........... | A61F 2/3609 433/173 |
| 2010/0051141 A1 * | 3/2010 | Bhambri | ........... | C21D 10/005 148/212 |
| 2014/0094927 A1 | 4/2014 | Weeden | | |
| 2014/0180425 A1 | 6/2014 | Katrana et al. | | |
| 2015/0216667 A1 | 8/2015 | Monaghan | | |
| 2017/0135820 A1 | 5/2017 | Muratoglu et al. | | |
| 2020/0129298 A1 * | 4/2020 | Kavolus, II | ........... | A61F 2/3609 |

OTHER PUBLICATIONS

Search Report for priority Italian Application No. 102019000014742, dated Apr. 30, 2020.

* cited by examiner

*Primary Examiner* — Brian A Dukert
(74) *Attorney, Agent, or Firm* — Egbert, McDaniel & Swartz, PLLC

(57) ABSTRACT

A hip prosthesis head includes: an external element with a convex external surface, and an internal element having a truncated-conical seat; wherein the external element and the internal element are made of different materials; the internal element is coupled in a blind hole of the external element in fit-in coupling mode; the external element has an annular base around the blind hole, and the internal element has a truncated-conical body that is open on the bottom, and an annular base that protrudes radially outwards from a lower edge of the body in order to be in contact with the base of the external element.

17 Claims, 27 Drawing Sheets

HIP PROSTHESIS HEAD

CROSS-REFERENCE TO RELATED APPLICATIONS

Not applicable.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The present invention relates to a hip prosthesis head.

2. Description of Related Art Including Information Disclosed Under 37 CFR 1.97 And 37 CFR 1.98.

Two types of hip replacements are known: total replacement (arthroprosthesis) and partial replacement (endoprosthesis).

Arthroprosthesis is a replacement of the arthrosic hip, deformed by necrosis or dysplasia or traumatic results. Unlike endoprosthesis, arthroprosthesis comprises a fixed acetabular component, which generally consists in a metal cup.

On the contrary, endoprosthesis consists in an implant that is entirely anchored in the femoral bone and is provided with a mobile acetabular dome with spherical convex shape that is joined with the pelvic bone, freely resting in an articular concavity, known as cotyloid cavity or acetabulum.

FIG. 1 shows an arthroprosthesis (101) according to the prior art.

The arthroprosthesis (101) comprises:

- a stem (3) suitable for being implanted in the femur of the patient;
- an acetabular cup (4) suitable for being implanted in the pelvic bone of the patient;
- a spherical head (105) fixed to the stem (3) by means of Morse taper coupling, and
- an insert (6) shaped like a spherical cap disposed between the head (105) and the acetabular cup (4), in such a way to permit a dual mobility between the head (105) and the insert (6), and between the insert (6) and the acetabular cup (4).

The insert (6), which is made of polyethylene, tends to wear out and becomes unable to slide in the acetabular cup (4), converting the prosthesis into a single mobility prosthesis.

FIG. 1A illustrates a single mobility arthroprosthesis (101') wherein the insert (6) is fixed to the acetabular cup (4) by means of a Morse taper system (conical surface (60) of the insert that is engaged in a conical surface (40) of the acetabular cup) or other fixing systems. The head (105) is coupled with the insert (6) in omnidirectional spherical coupling mode, with single mobility between the head (105) and the insert (6).

Being made of polyethylene and being subject to wear, the insert (6) must have a minimum thickness (for example, higher than 9 mm) to guarantee a long life. However, the large dimensions of the insert (6) impose a dimensional reduction of the head (105), which will be smaller than a real femoral bone head, with consequent drawbacks in terms of mobility.

FIG. 2 shows an endoprosthesis (102) according to the prior art.

The endoprosthesis (101) comprises:

- a stem (3) suitable for being implanted in the femur of the patient;
- a head (105) with spherical shape fixed to the stem (3) by means of Morse taper coupling, and
- an acetabular dome (7) disposed on the head (105) and inside the cotyloid cavity of the patient, in such a way to permit a dual mobility between the head (105) and the acetabular dome (7) and between the acetabular dome (7) and the cotyloid cavity of the patient.

The head (105) is press-fitted in the acetabular dome (7) in such a way that the head (105) cannot come out of the acetabular dome (7), causing a dislocation. Alternatively, the head (105) is disposed in the acetabular dome (7) and an elastic ring is disposed inside the acetabular dome, in such a way to expand and prevent the ejection of the head.

Currently, both the arthroprosthesis and the endoprosthesis comprise a head (105) that is made in one piece with one material, such as ceramics or metal. The metal prosthesis heads are generally made of steel or cobalt-chrome superalloy. The head (105) has a truncated-conical seat (150) that receives a truncated-conical shank (30) of the stem (3) in Morse taper coupling mode.

The prosthesis heads according to the prior art are impaired by drawbacks.

The hip prostheses with ceramic heads that are implanted in very big, heavy patients have proved to suffer a ceramic failure after a short time from surgery.

The hip prostheses with metal heads are impaired by the loss of metal ions, especially in case of metal-on-metal friction.

In case of hip prostheses with metal-on-metal coupling, and with head made of cobalt-chrome alloy, after a short time from surgery, cobalt-chrome ions have been found in the blood of patients because of to metallosis, with extremely severe health risks (see J&J Depuy lawsuit).

Moreover, the hip prostheses of the prior art are complicated and expensive because of the high number of components, and in particular because of the polyethylene insert that generates the aforementioned problems.

Furthermore, the elastic ring used in the prostheses of the prior art to prevent the ejection of the head has proved to be ineffective because it deteriorates with the risk of dislocation.

Additionally, it must be noted that in the hip prostheses of the prior art, when the head (105) is coupled with the stem (3), the axis of the shank (30) of the stem passes through the center of the head (105). Such an arrangement impairs the centering of the head (105) with respect to the center of rotation defined by the natural or artificial cotyloid cavity of the patient. Consequently, the dislocation of the hip prosthesis may occur.

Moreover, the external surface of the head is shaped like a spherical cap and such a type of surface cannot be not perfectly coupled with the cotyloid cavity of the patient in case of endoprosthesis.

US2014/180425 discloses a hip prosthesis comprising a head composed of a metal substrate and a polymer coating. The metal substrate can be made of cobalt-chrome and/or titanium. The polymer coating can be made of PEEK or HXPLE. The metal substrate has a base that is embedded in the polymer coating. The base has an undercut flange that prevents a fit-in coupling between metal substrate and polymer coating. Consequently, the realization of such a prosthesis head is complicated because it requires the co-molding of the polymer coating on the metal substrate and the prosthetic head is not versatile.

US2014/094927 discloses a hip prosthesis comprising a head made of PEEK or cross-linked polyethylene. Such a head has a seat wherein a truncated-conical insert is inserted, it being suitable for receiving a stem for anchoring to a femur. Such an insert has a lower edge, without a base. The lower edge of the insert protrudes from the bottom of the head; otherwise said, a considerable distance is provided between the lower edge of the insert and the head. The portion of the insert that projects from the head involves problems in terms of reliability and stability of the prosthesis, as well as difficulties in the installation during surgery.

BRIEF SUMMARY OF THE INVENTION

The purpose of the present invention is to eliminate the drawbacks of the prior art by disclosing a hip prosthesis head that is reliable, safe, versatile and easy to make.

Another purpose of the present invention is to disclose such a hip prosthesis head that can be easily installed by the surgeon and allows for using a prosthesis with a minimum number of components.

These purposes are achieved according to the invention with the characteristics of the independent claim 1.

Advantageous embodiments of the invention appear from the dependent claims.

The hip prosthesis head according to the invention is defined by claim 1.

BRIEF DESCRIPTION OF THE SEVERAL VIEWS OF THE DRAWINGS

Additional features of the invention will be clearer from the following detailed description, which refers to merely illustrative, not limiting embodiments, as shown in the appended figures, wherein.

DETAILED DESCRIPTION OF THE INVENTION

Figure 1:
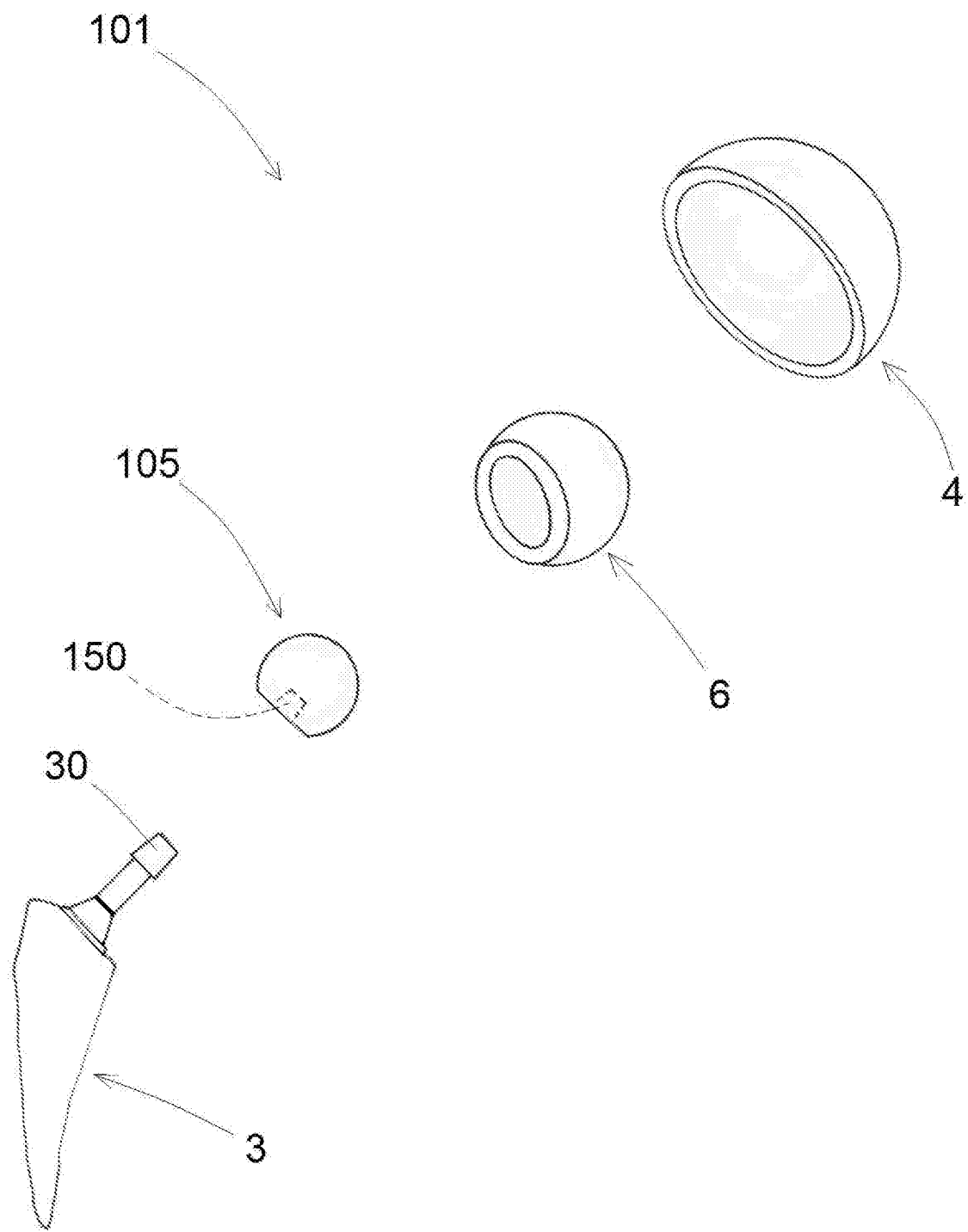
FIG. 1 is an exploded perspective view of a dual mobility arthroprosthesis according to the prior art.
Figure 1A:
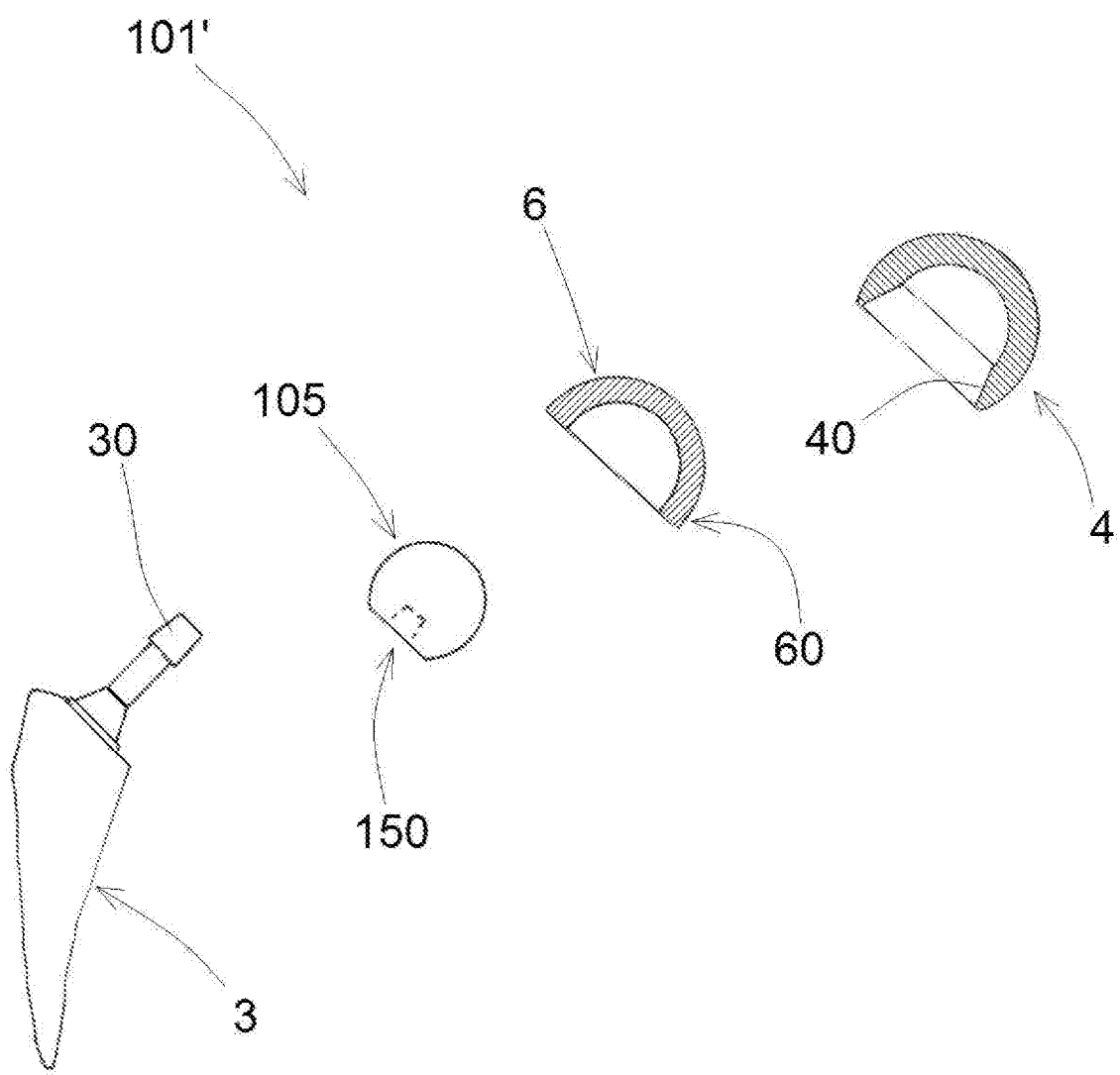
FIG. 1A is an exploded perspective view of a single mobility arthroprosthesis according to the prior art.
Figure 2:
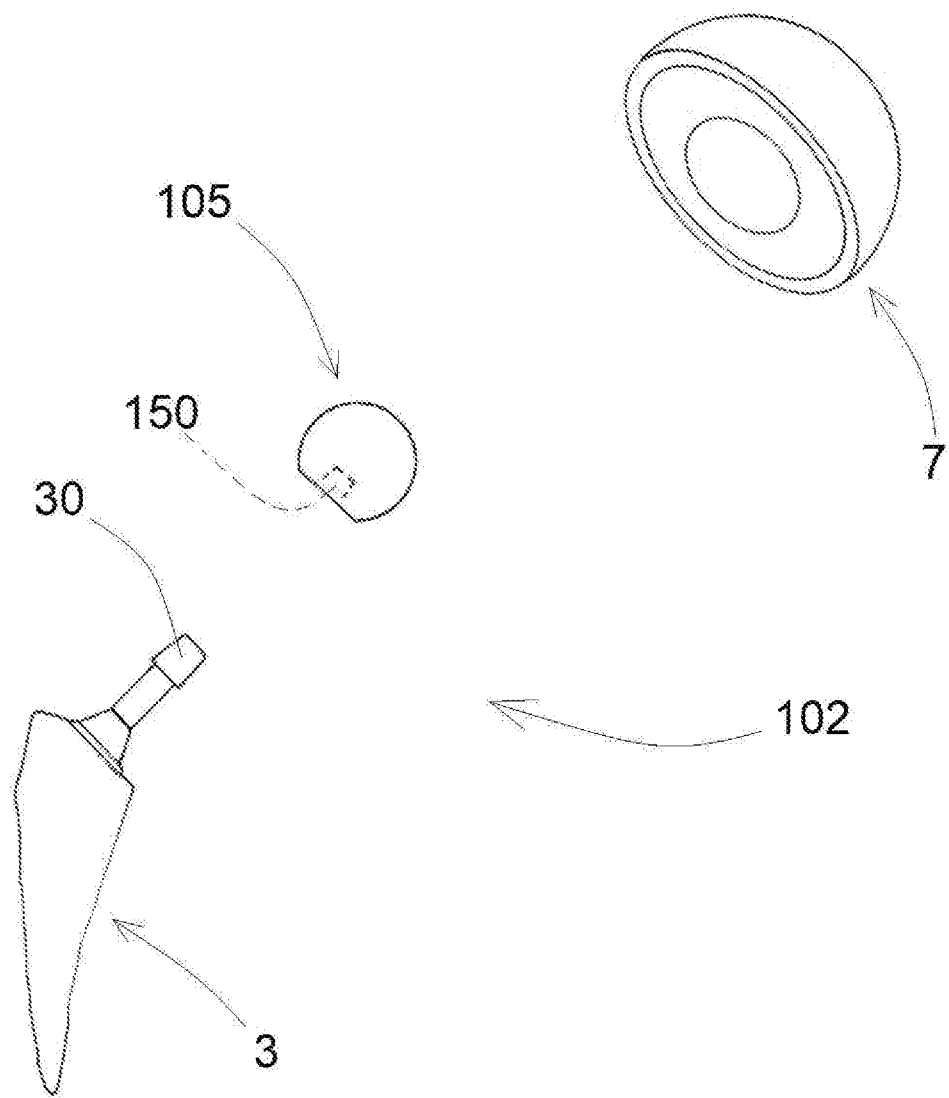
FIG. 2 is an exploded perspective view of an endoprosthesis according to the prior art.

In the following description, elements that are identical or correspond to the ones described above will be indicated in the drawings with the same numerals, omitting a detailed description.

Figure 3:
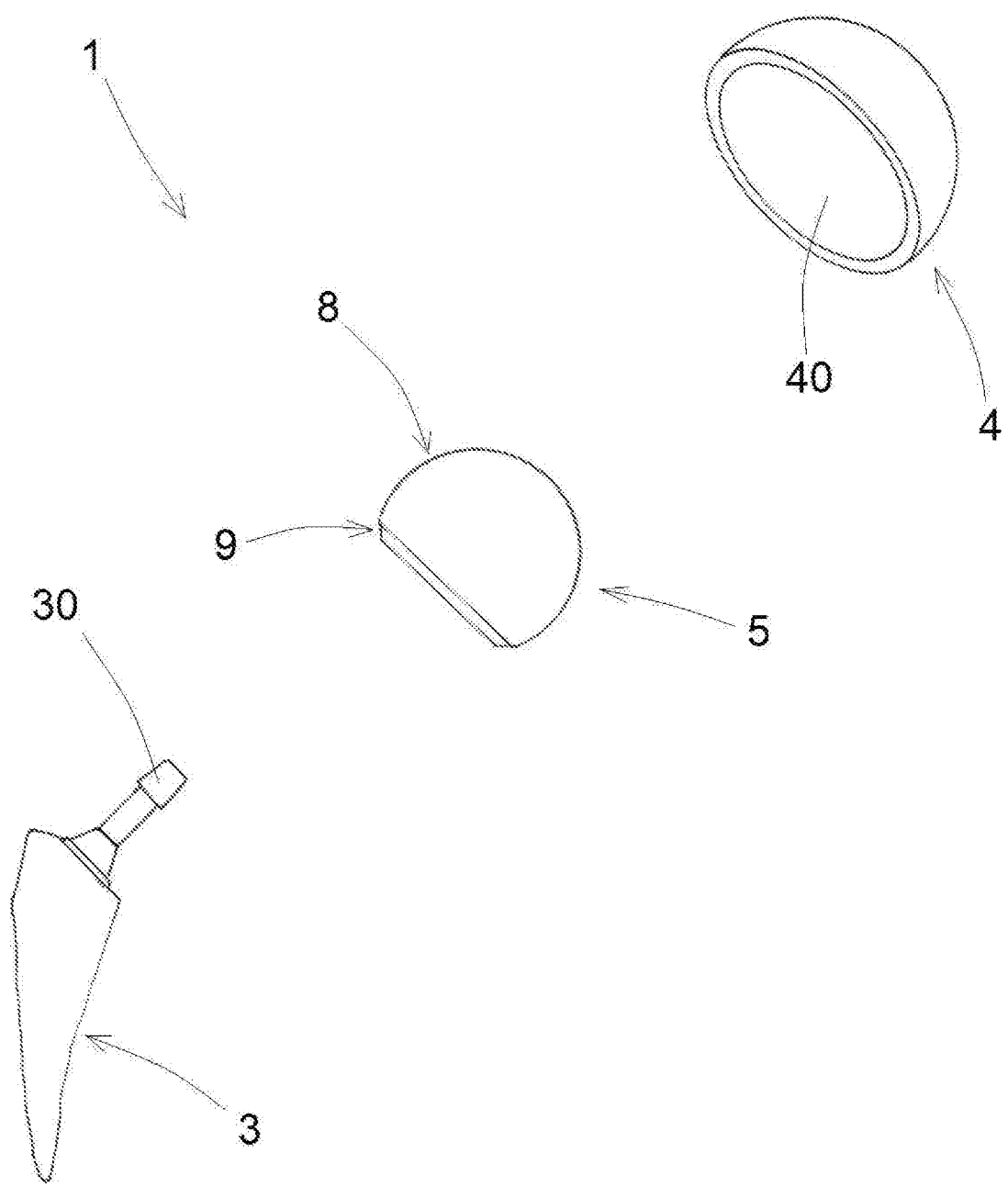
FIG. 3 is an exploded perspective view of an arthroprosthesis provided with a head according to a first embodiment of the invention.

FIG. 3 shows an arthroprosthesis (1) provided with a head (5) according to a first embodiment of the invention.

With reference to FIGS. 4, 5, 6 and 7, the head (5) comprises two components: an external element (8) and an internal element (9) made of different materials.

The external element (8) is made of a plastic material, such as cross-linked polyethylene (PEX, XPE or XLPE) o of a technopolymer, such as polyether-ether-ketone (PEEK).

Advantageously, the external element (8) is made of vitamin E-enriched cross-linked polyethylene.

The internal element (9) is made of a metal material, such a medical steel or cobalt-chrome superalloy or titanium. Advantageously, the internal element (9) can be made of a metal material coated with nitrided titanium.

Figure 6:
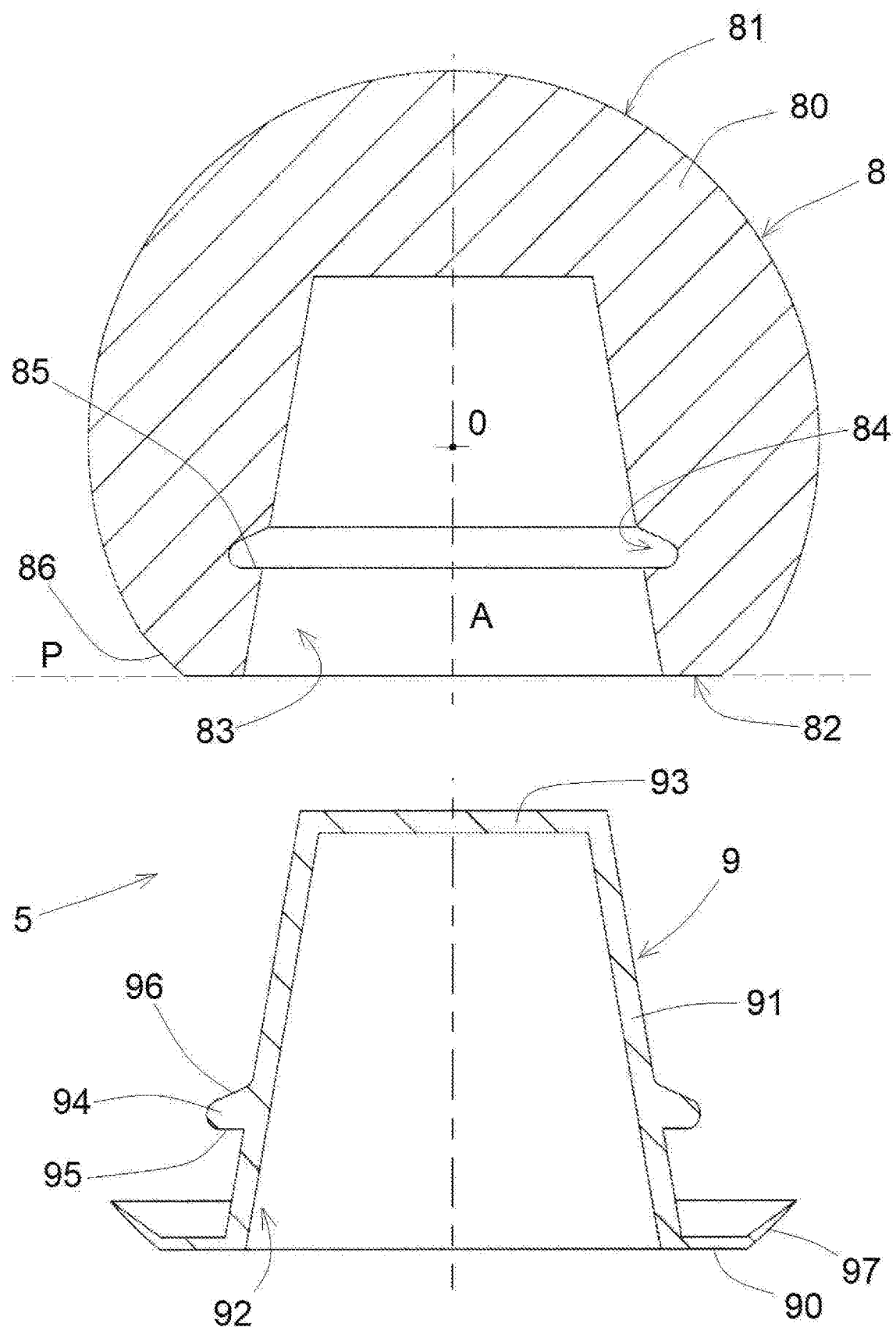
FIG. 6 is an exploded axial view of the head of FIG. 4.
Figure 7:
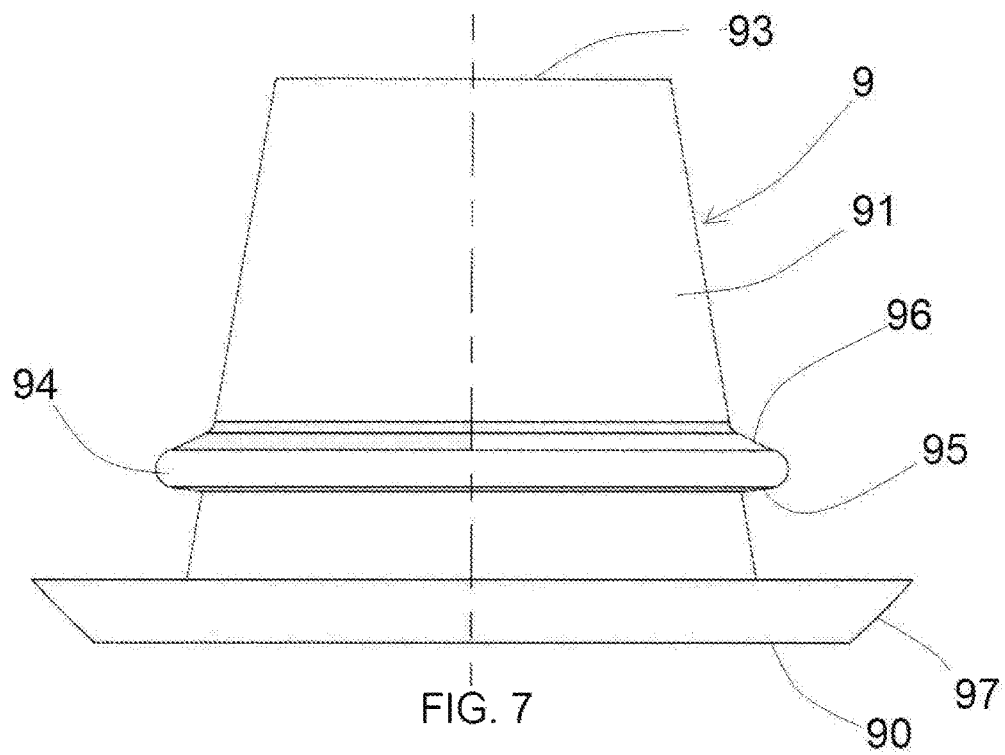
FIG. 7 is a side view of an internal element of the head of FIG. 5.
Figure 8:
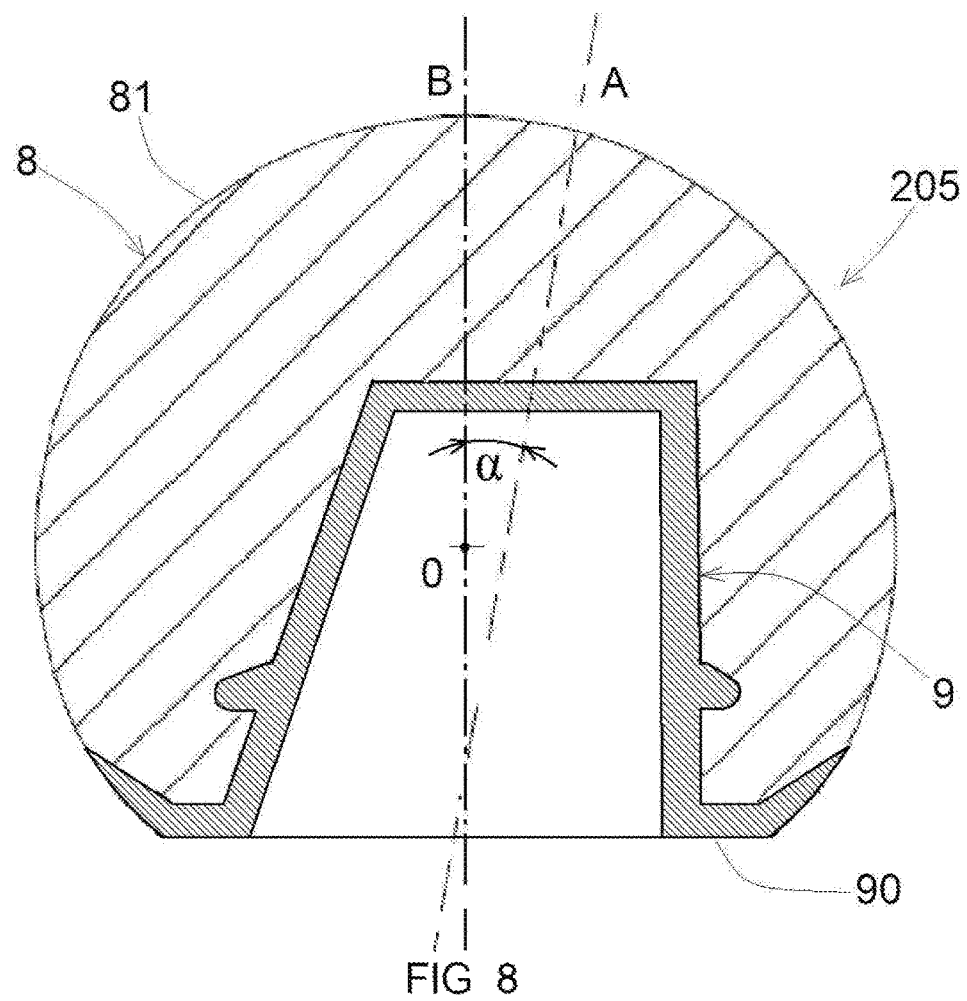
FIG. 8 is an axial view of a head for arthroprosthesis according to a second embodiment of the invention.
Figure 9:
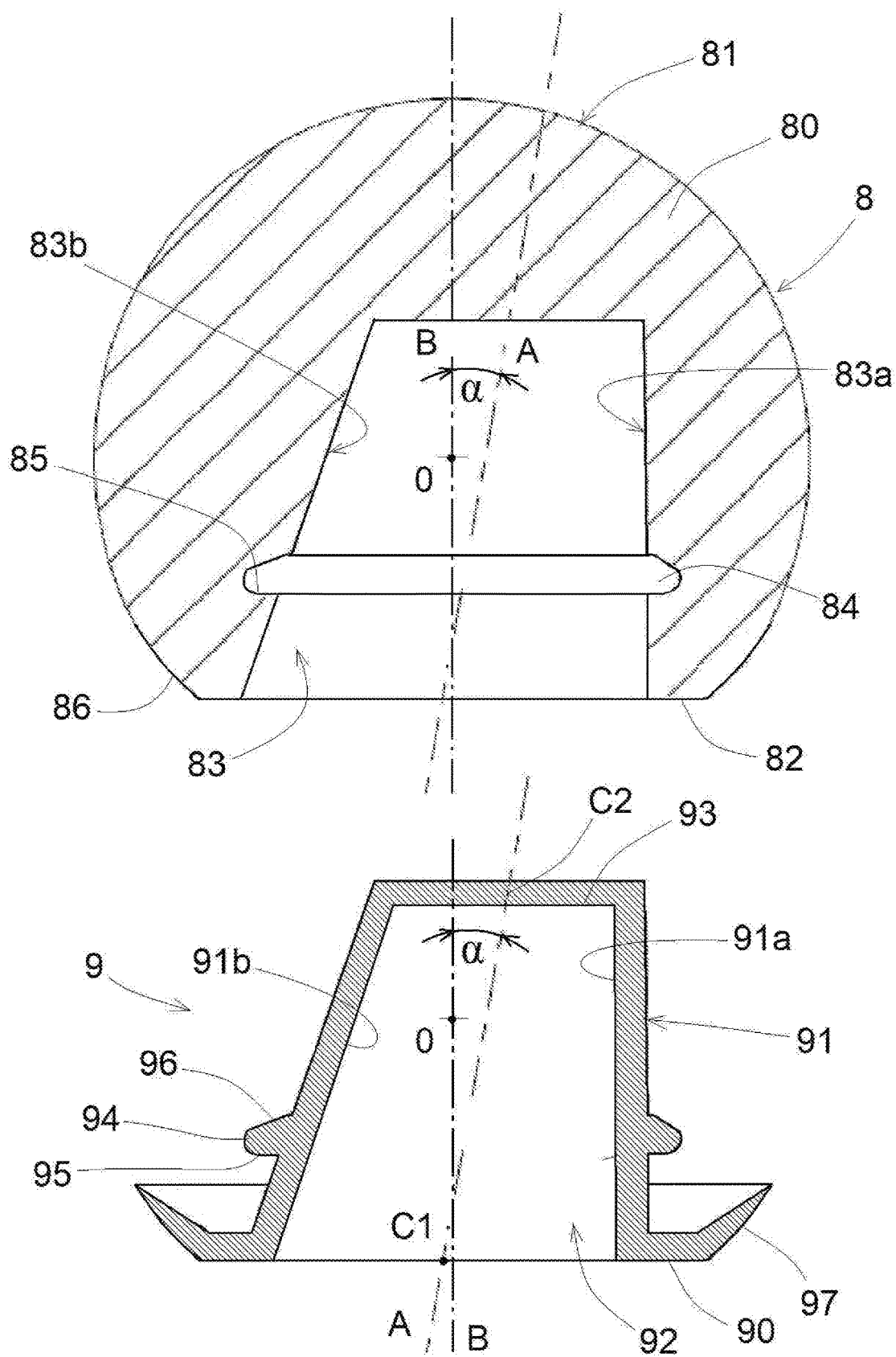
FIG. 9 is an exploded axial view of the head of FIG. 8.
Figure 10:
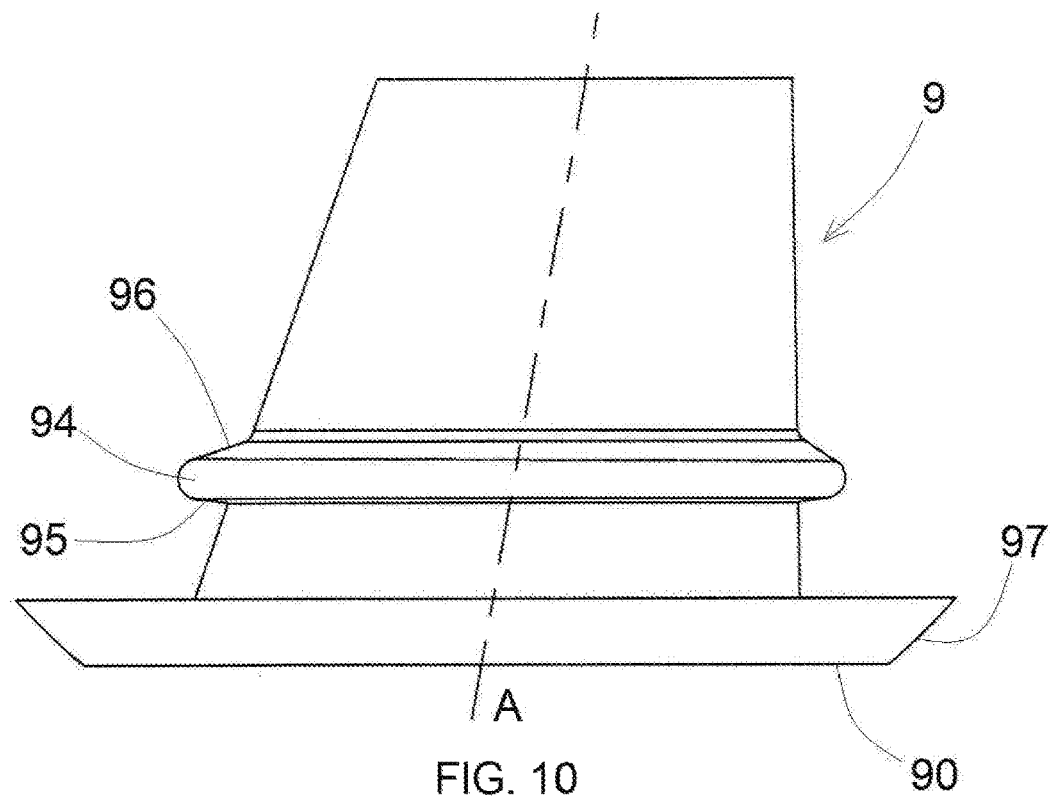
FIG. 10 is a side view of an internal element of the head of FIG. 8.

With reference to FIG. 6, the external element (8) comprises a body (80) with an external surface (81) with convex shape, like a spherical cap, with center (O), cut at the height of a parallel (P) at approximately 30-40° south in such a way to define a planar base (82).

The external surface (81) of the external element is suitable for coupling with an internal surface (40) with concave shape of the acetabular cup (4) (FIG. 3) in omnidirectional spherical coupling mode. It must be noted that the internal surface (40) of the acetabular cup can be made of metal material. In fact, in such a case, the metal material of the acetabular cup slides on the external element (8) made of plastic of the head, avoiding metal-on-metal friction. Moreover, in such a way the use of an additional component, such as the insert (6) (FIG. 1) of the arthroprosthesis (101) of the prior art, is avoided.

Figure 3A:
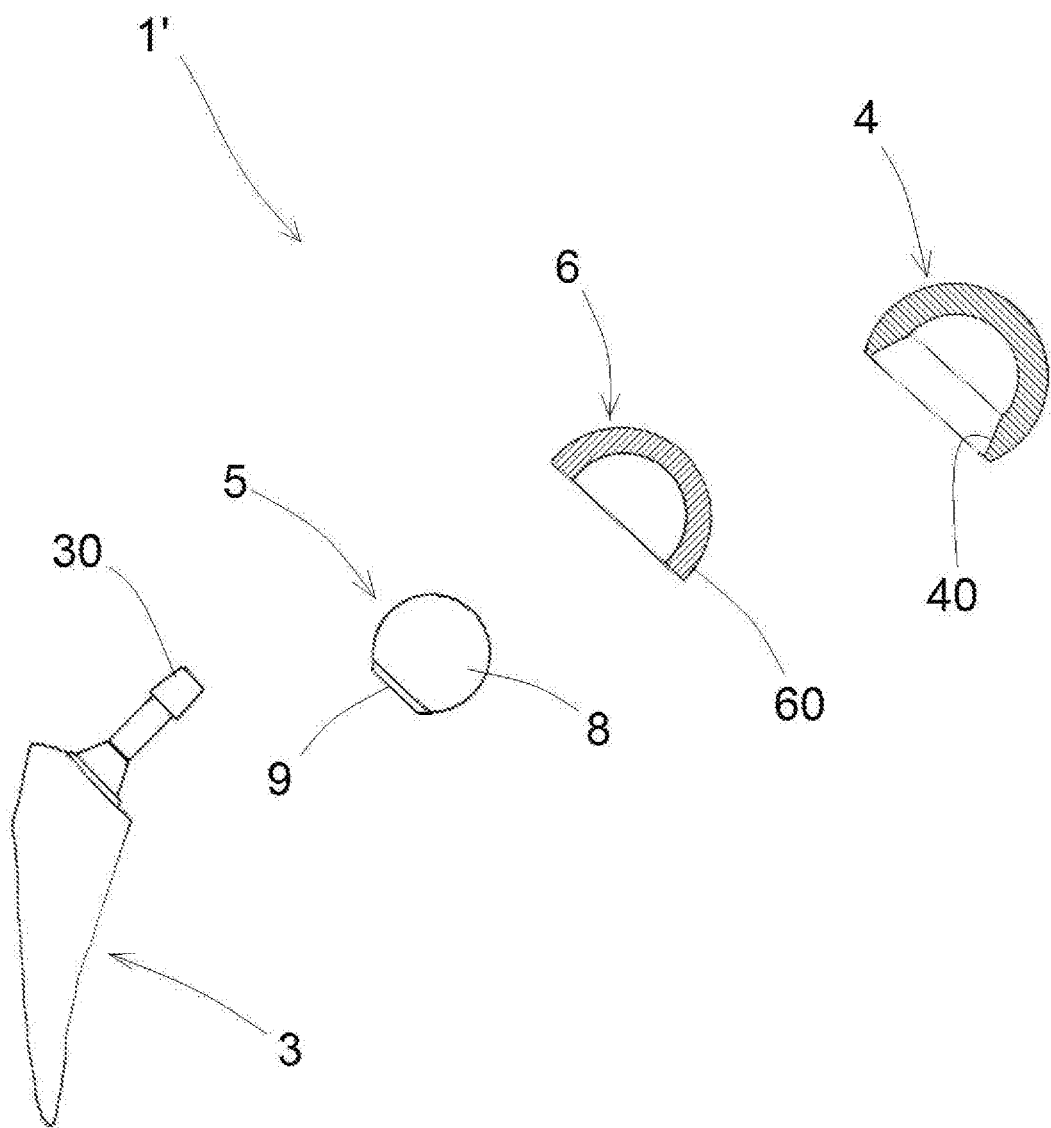
FIG. 3A is a diagrammatic view in partially axial section that shows a single mobility arthroprosthesis provided with a head according to a first embodiment of the invention.
Figure 4:
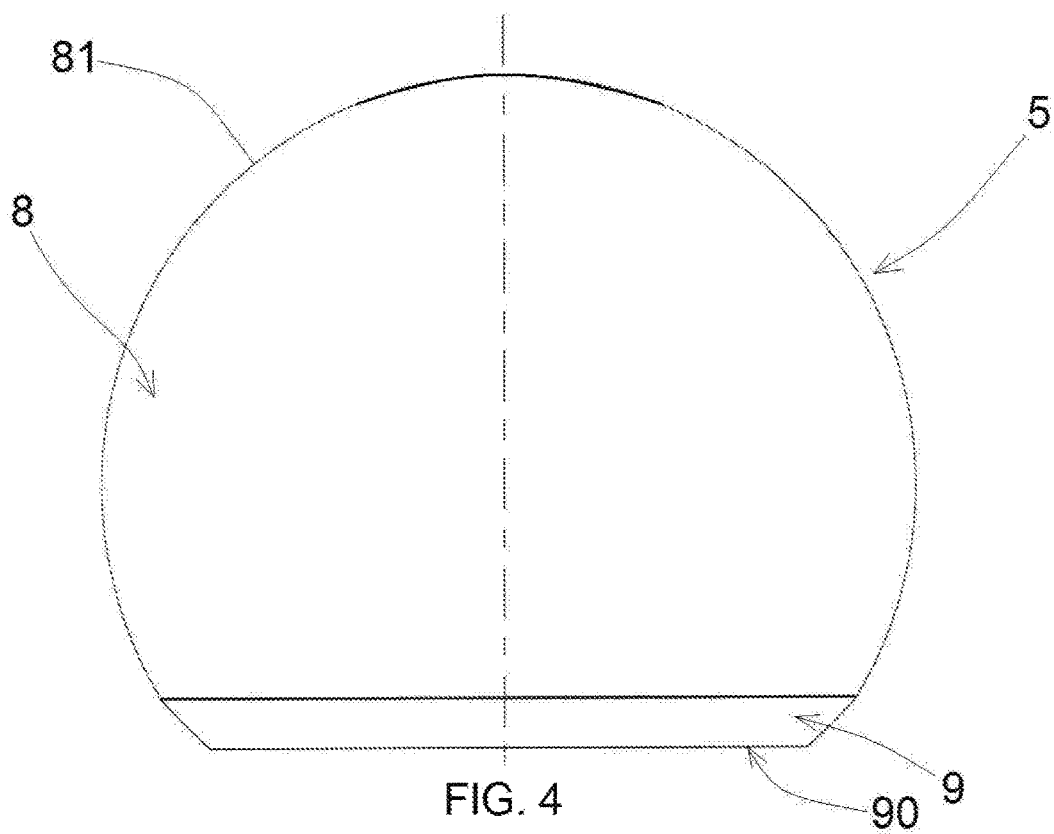
FIG. 4 is a side view of the head of the arthroprosthesis of FIG. 3.

FIG. 3A shows a single mobility arthroprosthesis (1') provided with the head (5) of the invention. In such a case, the insert (6) can be made of metal material or ceramic because the insert (6) is fixed to the acetabular cup (4) and the external element (8) of the head (5) that slides on the insert (6) is made of cross-linked polyethylene or PEEK, so that no metal-on-metal friction is produced and the head (5) acts as shock-absorber for the insert (6), thus ensuring its longer life.

Being made of metal, the insert (6) can have a reduced thickness (for example, lower than 9 mm). Consequently, the head (5) can have higher dimensions than the head (105) of the prior art, in such a way to reproduce the real dimensions of a femoral bone head.

A Morse tapered blind hole (83) with truncated-conical shape, with an axis (A) orthogonal to the base (82) and passing through the center (O) is obtained in the base (82) of the external element. The height of the blind hole (83) is higher than half of the height of the external element (8), in such a way that the center (O) is contained within the blind hole (83).

An annular groove (84) shaped like a collar is obtained in the blind hole (83), in intermediate position between the base (82) and the center (O). The annular groove (84) has a lower surface (85) shaped like a radial step relative to the axis (A).

The base (82) is joined to the external surface (81) by means of a tapered annular edge (86) with increasing dimensions going from the base (82) towards the external surface (81).

The internal element (9) is suitable for being coupled inside the blind hole (83) of the external element (8), in fit-in coupling mode, in such a way that the external element (8) and the internal element (9) are integrally fixed.

The internal element (9) has a base (90) shaped like an annular plate, from which an internally empty truncated-conical body (91) stands out, in such a way to define a truncated-conical housing (92) that is open in the base (90). The body (91) is closed on top by an upper wall (93). Otherwise said, the base (90) radially protrudes outwards from a lower edge of the body (91).

An annular rib (94) shaped like a collar protrudes externally from the body (91) of the internal element. The annular rib (94) has a lower surface (95) that is radial and parallel to the lower surface (85) of the annular groove (84) of the external element, and a tapered upper surface (96) in order not to damage the cross-linked polyethylene of the external element during the insertion of the internal element.

The base (90) of the internal element has a peripheral tapered edge with increasing dimensions going from the base (90) upwards that forms an annular rib (97).

The internal element (9) is forcedly inserted in the blind hole (83) of the external element (8). The upper surface (96) of the annular rib (94) of the internal element slides on the internal surface of the blind hole (83) of the external element. During such a sliding movement, the external element (8) made of plastic and the internal element (9) with a body (91) with a reduced thickness of approximately 1 mm, suffer an elastic deflection until the annular rib (94) of the internal element penetrates the annular groove (84) of the external element.

Figure 5:
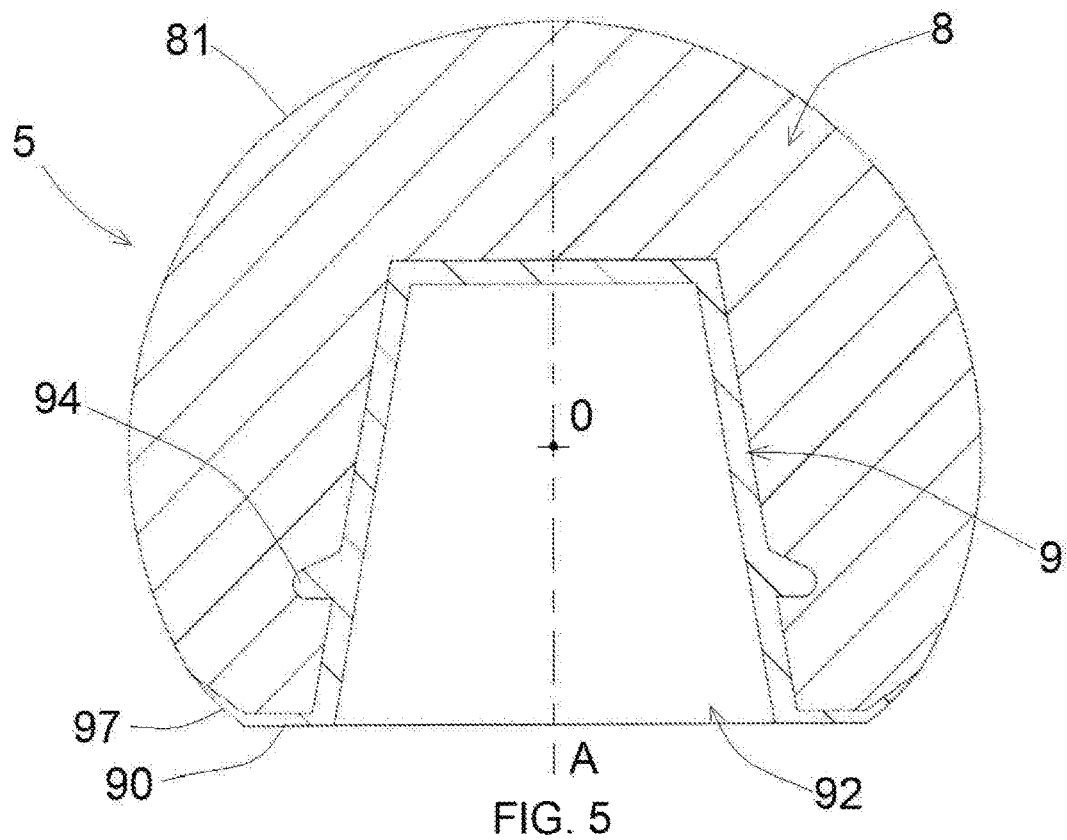
FIG. 5 is an axial view of the head of FIG. 4.

In such a situation, as shown in FIG. 5, the upper wall (93) of the internal element is in contact with an upper wall of the blind hole (83) of the external element, the base (90) of the internal element is in contact with the base (82) of the external element and the annular rib (97) of the base of the internal element is in contact with the annular edge (86) of the external element.

The internal element (9) can no longer be extracted from the external element (8) because the lower surface (95) of the annular rib (94) of the internal element is in contact with the lower surface (85) of the annular groove (84) of the external element.

It must be noted that, when the internal element (9) is coupled with the external element (8), the axis (A) of the truncated-conical housing (92) of the internal element coincides with the axis of the blind hole (83) of the external element, which passes through the center (O) of curvature of the external surface (91) of the external element and is orthogonal to the base (90) of the internal element.

The truncated-conical housing (92) of the internal element is suitable for receiving the truncated-conical shank (30) of the stem (3) (FIG. 3) in Morse tapered coupling mode. Since the truncated-conical shank (30) of the stem is made of metal and also the internal element (9) of the head is made of metal, a perfect Morse tapered coupling is provided between the stem and the head.

FIGS. 8-12 show a head (205) for arthroprosthesis according to a second embodiment.

The head (205) has an external element (8) with a blind hole (83) with an irregular truncated-conical shape, with a rectangular trapezoidal section, i.e. the blind hole (83) has a cylindrical portion (83a) joined to a truncated-conical portion (83b).

A normal axis (B) orthogonal to the base (92) of the external element and passing through the center (O) of curvature of the external surface (81) of the external element is defined. It must be noted that the axis (A) of the blind hole (93) of the external element is inclined by an angle ( ) relative to the normal axis (B). The angle ($\alpha$) varies from approximately 5 to 20°.

It must be noted that, when the internal element (9) is coupled with the external element (8), the axis (A) of the truncated-conical housing (92) of the internal element coincides with the axis of the blind hole (83) of the external element. The axis (A) of the truncated-conical seat (92) is defined as the axis passing through the center (C1) of the hole of the truncated-conical housing (92) in the base (90) and center (C2) of the upper wall (93) of the internal element. The axis (A) of the truncated-conical housing (92) of the internal element is inclined by an angle ( ) relative to the normal axis (B) orthogonal to the base (90) of the internal element and passing through the center (O) of curvature of the external surface (91) of the external element. The truncated-conical housing of the internal element has an irregular truncated-conical shape, with a rectangular trapezoidal section, with a cylindrical portion (91a) that is joined to a truncated-conical portion (91b).

Such a shape of the truncated-conical housing (93) with an inclined axis (A) relative to the normal axis (B) provides an easier coupling with a truncated-conical shank of the stem (3) suitable for being implanted in the femur.

Figure 13:
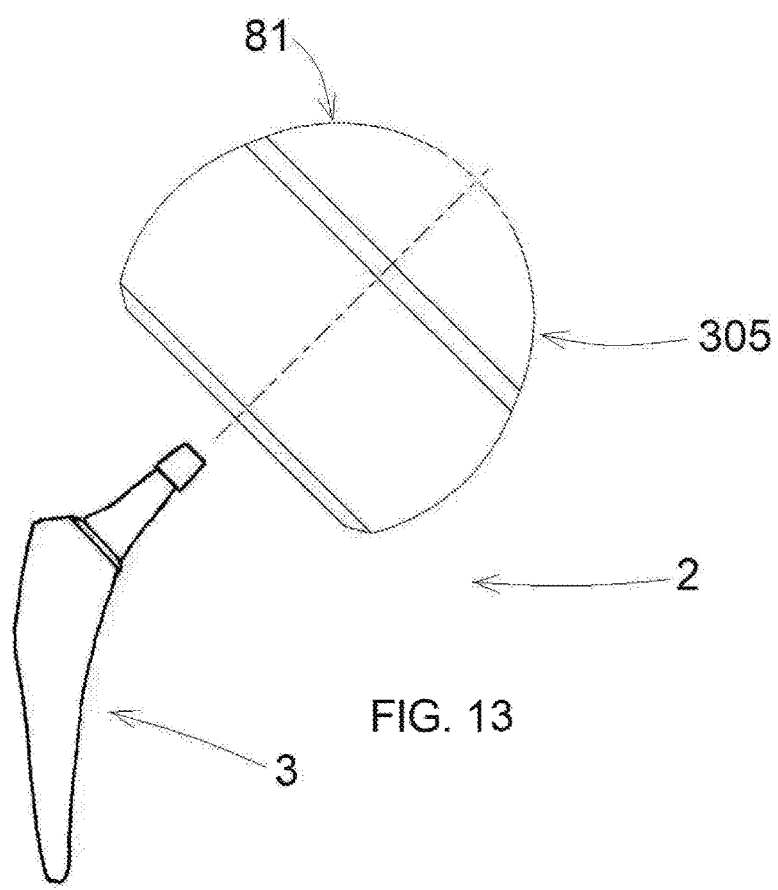
FIG. 13 is an exploded perspective view of an endoprosthesis provided with a head according to a third embodiment of the invention.
Figure 11:
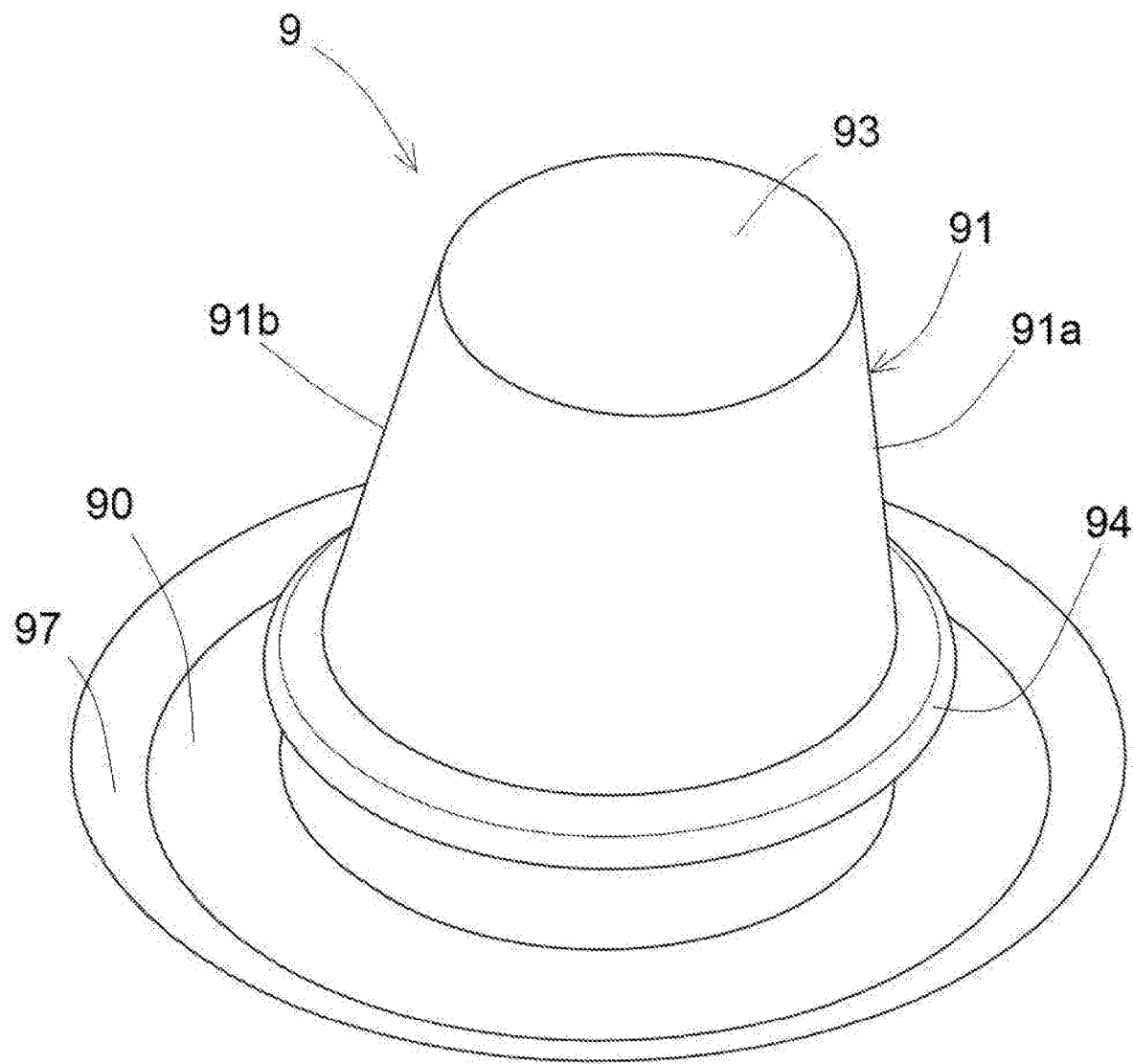
FIG. 11 is a perspective view of the internal element of the head of FIG. 8.
Figure 12:
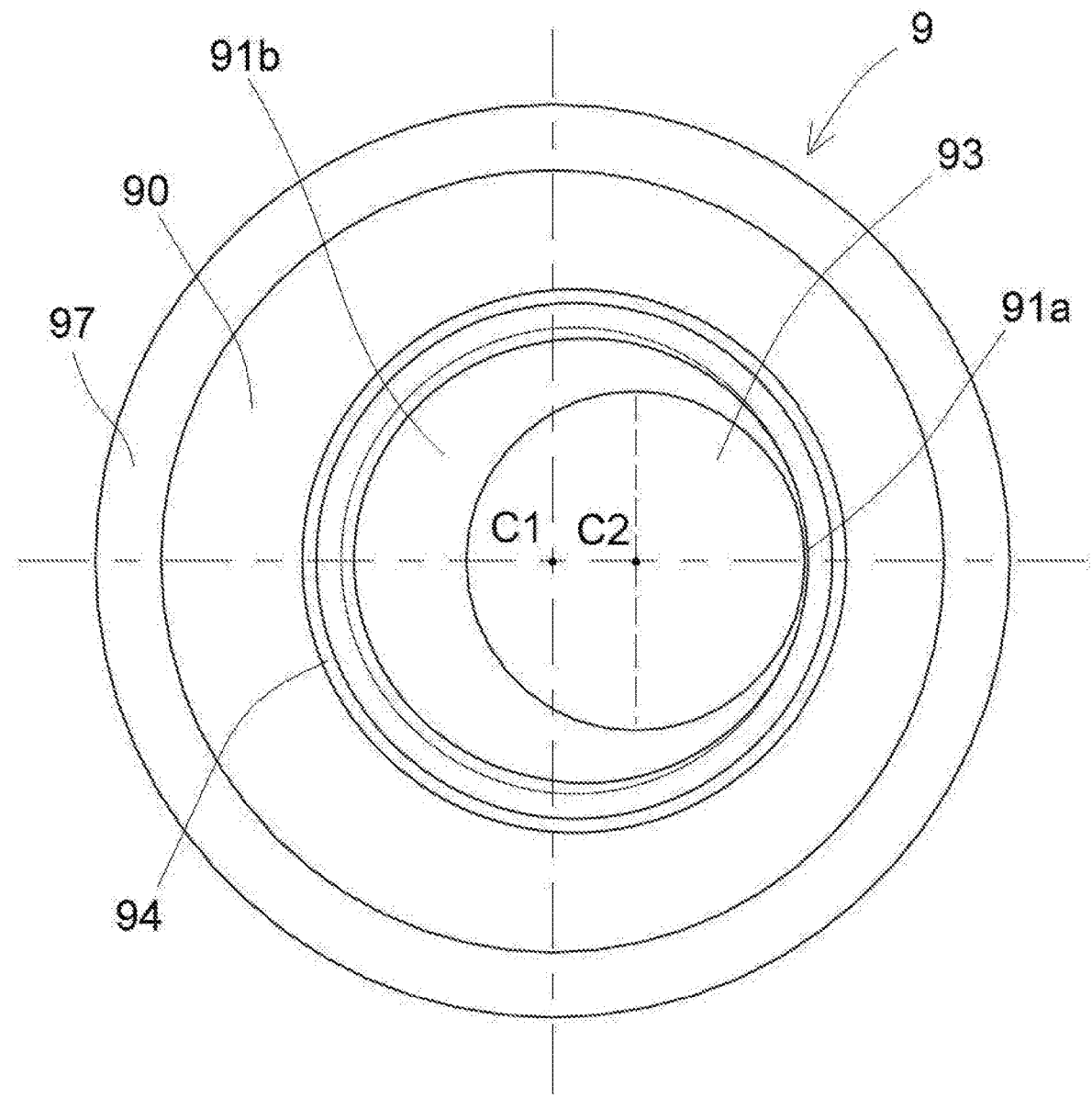
FIG. 12 is a top view of the internal element of the head of FIG. 8.
Figure 14:
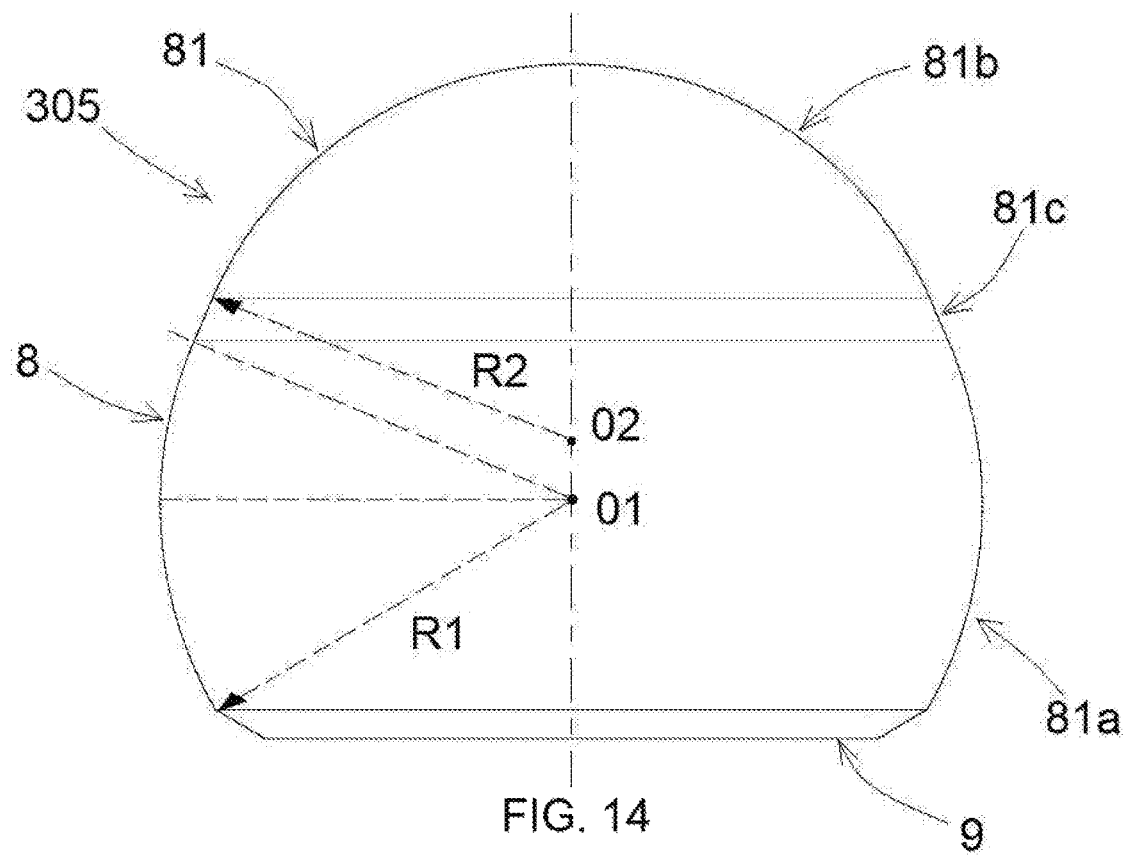
FIG. 14 is a side view of the head of the endoprosthesis of FIG. 13.

FIG. 13 shows an endoprosthesis (2) with a head (305) according to a third embodiment of the invention. In such a case, the head (305) has a convex external surface (81) suitable for being movably coupled directly inside a concave seat of a cotyloid cavity of the patient.

FIGS. 14-17 show the head (305) of the third embodiment.

The external element (8) has an external surface (81) that comprises three portions:
a lower portion (81a) shaped like a cap portion,
an upper portion (81b) shaped like a cap, and
an intermediate portion (81c) with truncated-conical shape that joins the lower portion to the upper portion.

Figure 17:
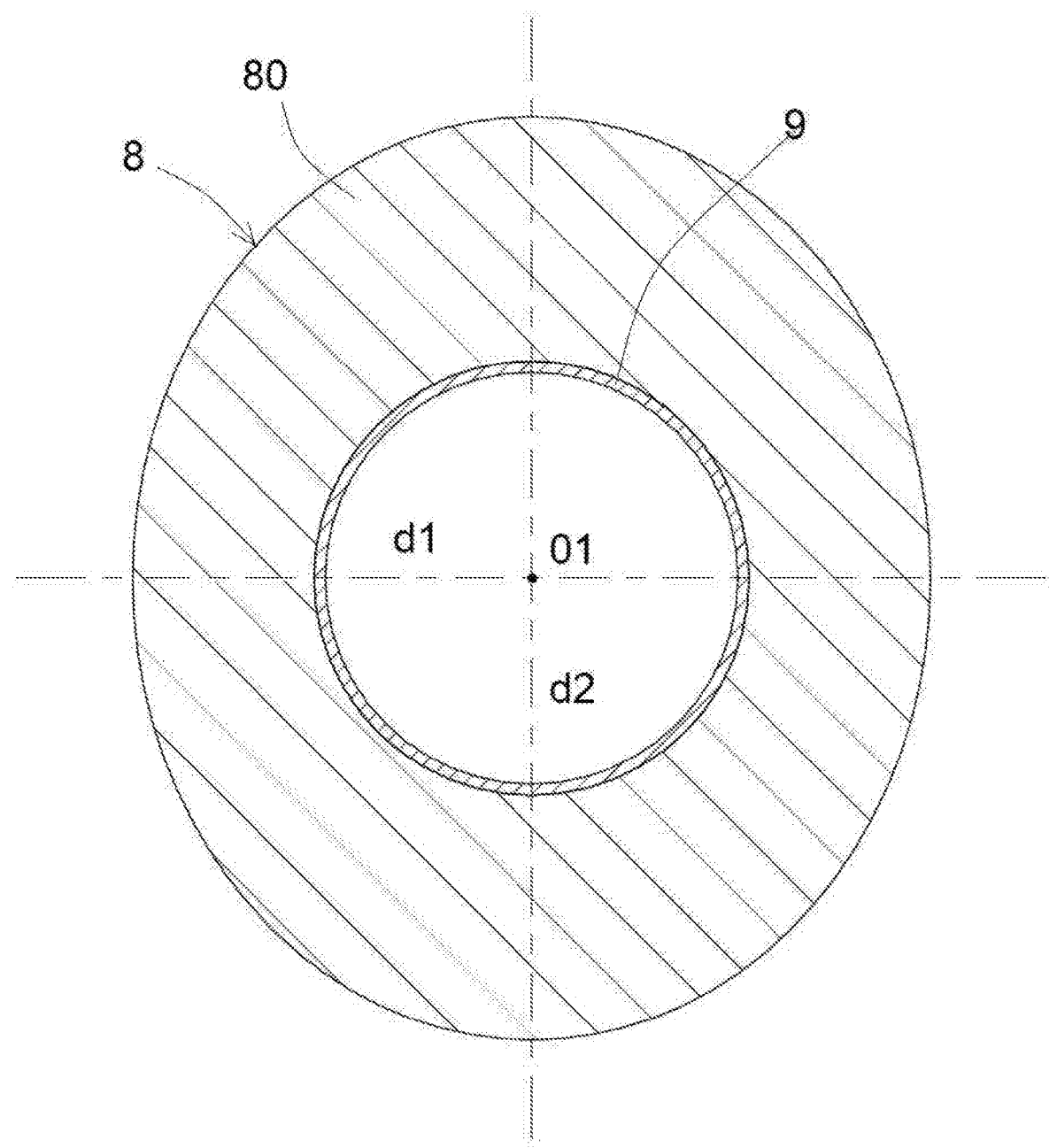
FIG. 17 is a cross-sectional view of the head of FIG. 14.

With reference to FIG. 17, each portion (81a, 81b, 81c) of the external element has an elliptical cross-section with a minor axis (d1) and a major axis (d2) longer than the minor axis by approximately 1-3 mm. In fact, generally speaking, the cotyloid cavity of the patient has a shape with an elliptical cross-section, and not a perfectly spherical shape.

Figure 15:
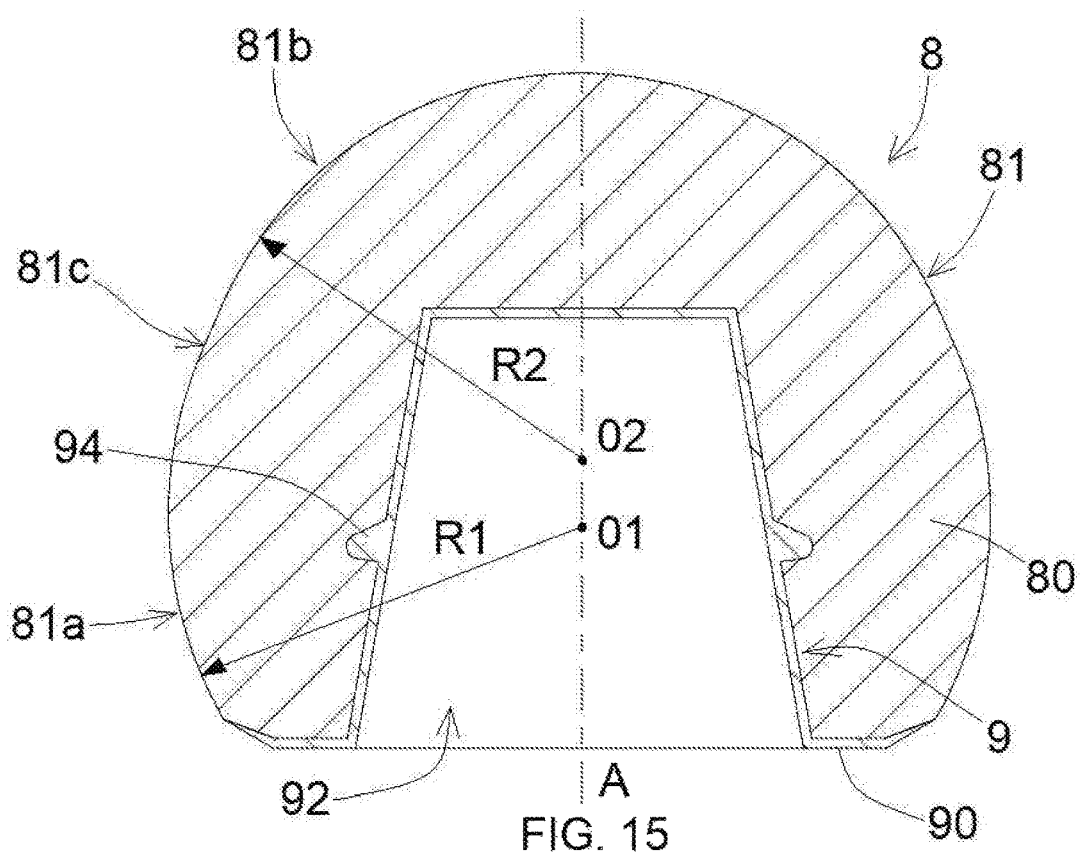
FIG. 15 is an axial view of the head of FIG. 14.
Figure 16:
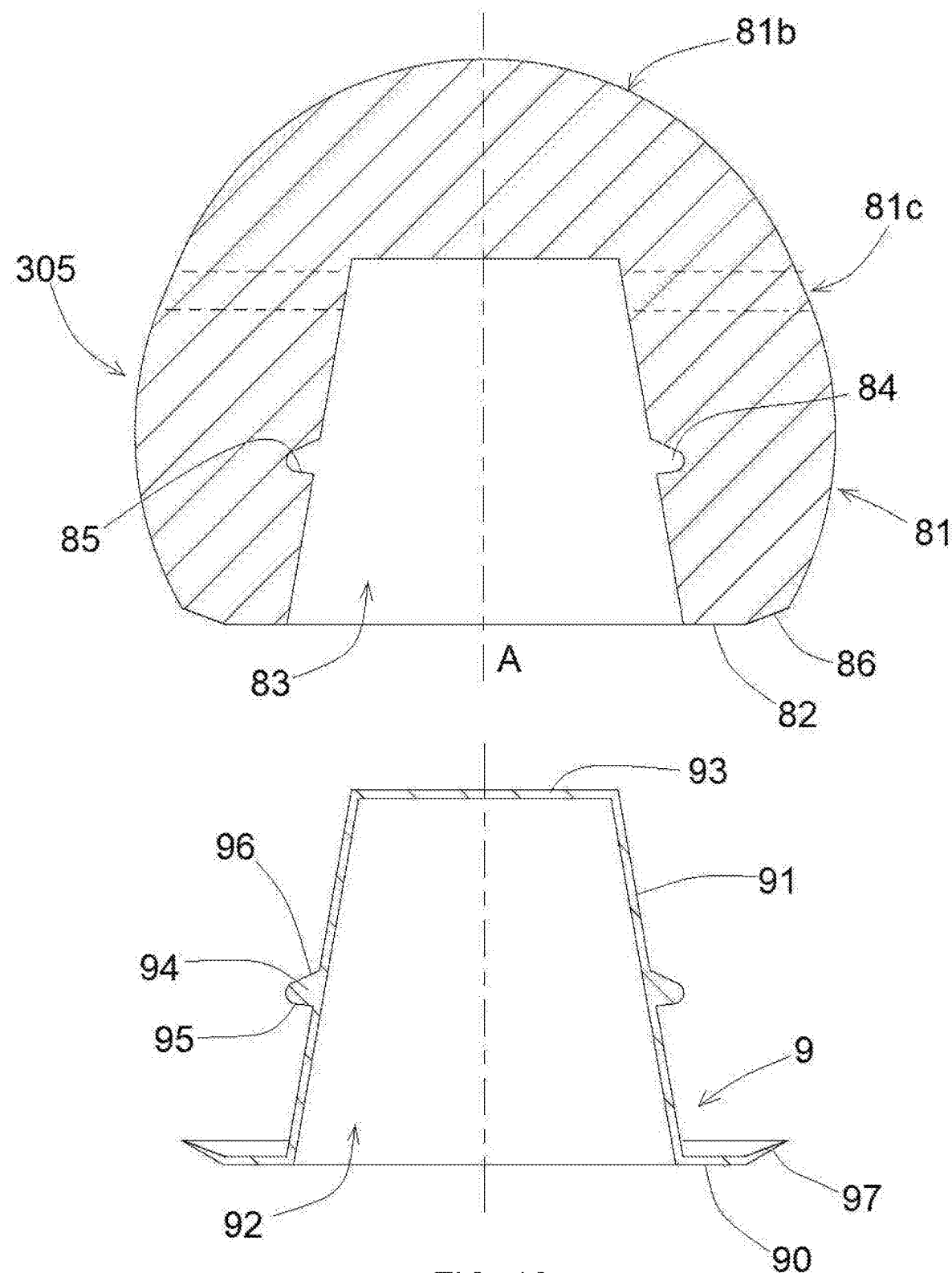
FIG. 16 is an exploded axial view of the head of FIG. 14.

With reference to FIG. 15, in axial section, the lower portion (81a) has a center (O1) and a radius of curvature (R1) and is cut at the height of a parallel 30° South and a parallel 20° North.

In axial section, the upper portion (81b) has a center (O2) and a radius of curvature (R2) and is cut at the height of a parallel 20° North.

The radius of curvature (R2) of the upper portion is smaller than the radius of curvature (R1) of the lower portion.

The center (O1) of the lower portion and the center (O2) of the upper portion are disposed on the axis (A) of the blind hole (83) of the external element that coincides with the axis of the housing (92) of the internal element.

The center (O2) of the upper portion is spaced on top relative to the center (O1) of the lower portion.

The radius of curvature (sR1) of the lower portion is slightly larger than the radius of curvature (R2) of the upper portion.

The intermediate portion (81c) has a height lower than the radius of curvature (R2) of the upper surface by approximately 8-10 times.

Such a configuration of the external surface (81) of the external element provides a better mobile coupling between the external surface (81) of the external element and the concave surface defined by the cotyloid cavity of the patient because the external element has an elliptical cross-section and because the external element has two cap-shaped portions with spaced-out centers of curvature.

Figure 18:
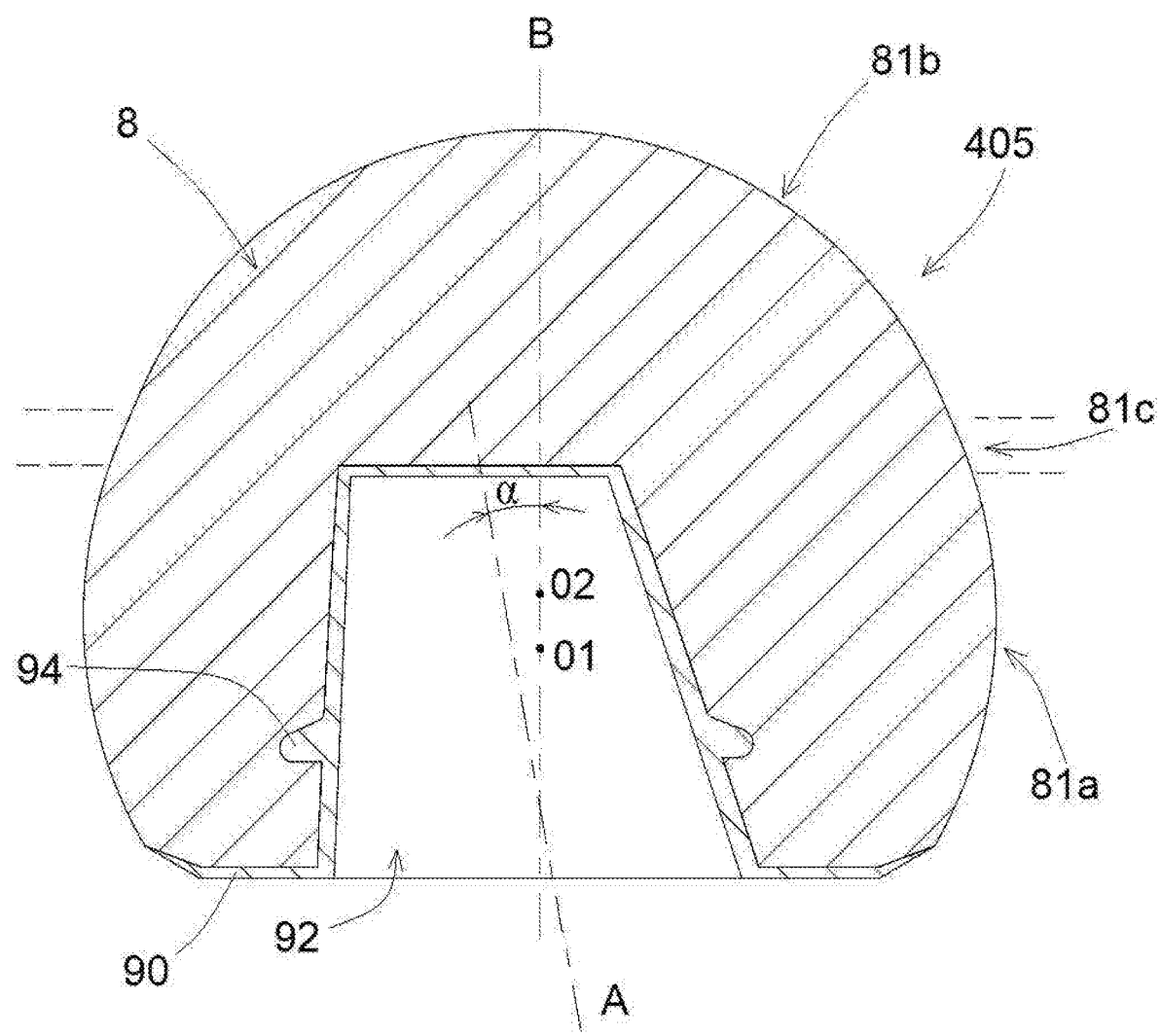
FIG. 18 is an axial view of a head for endoprosthesis according to a fourth embodiment of the invention.
Figure 19:
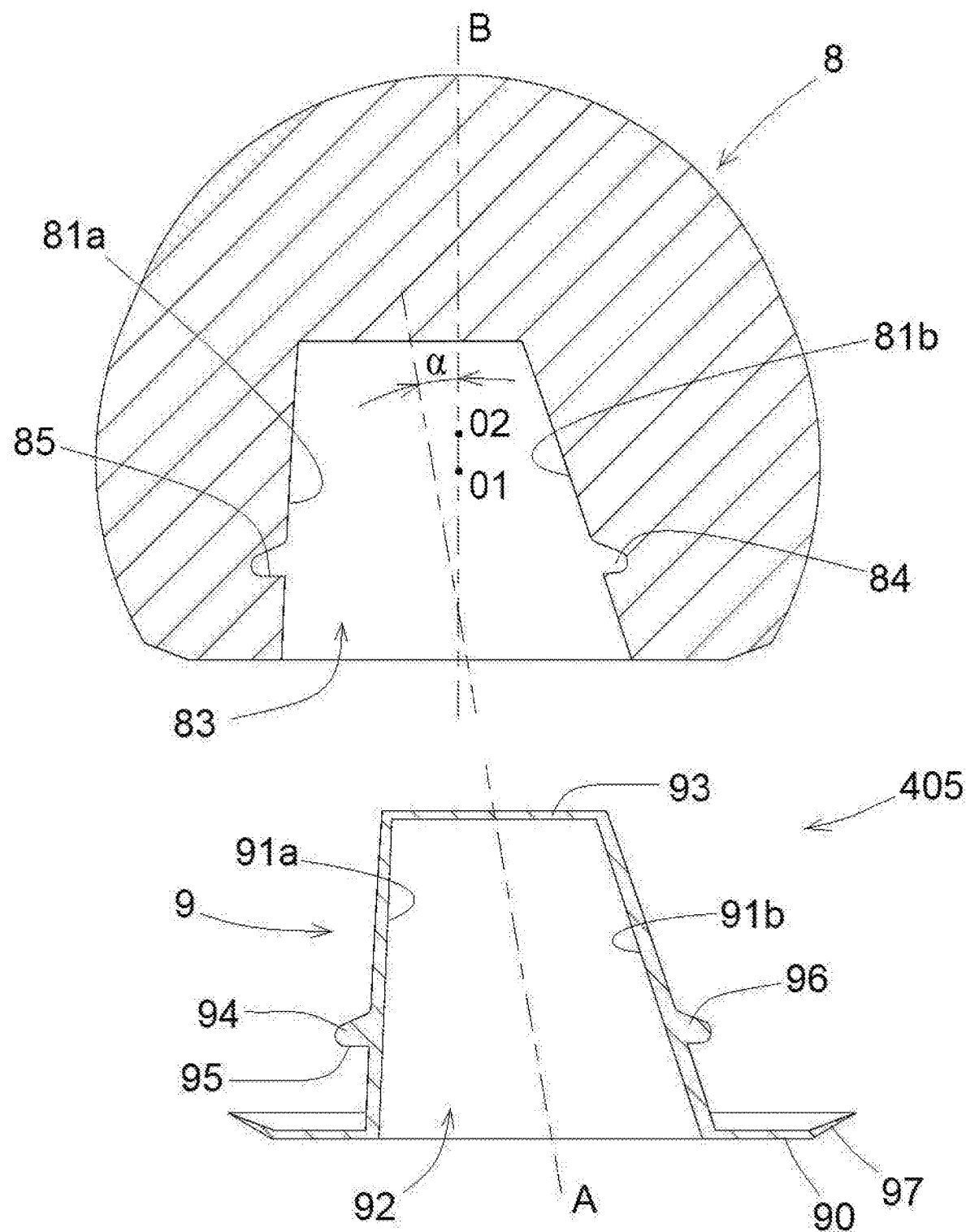
FIG. 19 is an exploded axial view of the head of FIG. 18.

FIGS. 18 and 19 show a prosthetic head (405) according to a fourth embodiment.

The prosthetic head (405) has an external element (8) with an external surface that is identical to the one of the external element of the prosthetic head (305) of the third embodiment, and an internal element (9) that is identical to the internal element of the prosthetic head (205) of the second embodiment.

In such a case, the center (O1) of the lower portion and the center (O2) of the upper portion of the external surface of the external element are disposed on the normal axis (B) orthogonal to the base (82) of the external element and to the base (90) of the external element.

The axis (A) of the blind hole (83) of the external element and of the housing (92) of the internal element is inclined by an angle ($\alpha$) relative to the normal axis (B). The angle ( ) varies from approximately 5 to 20°.

Figure 20:
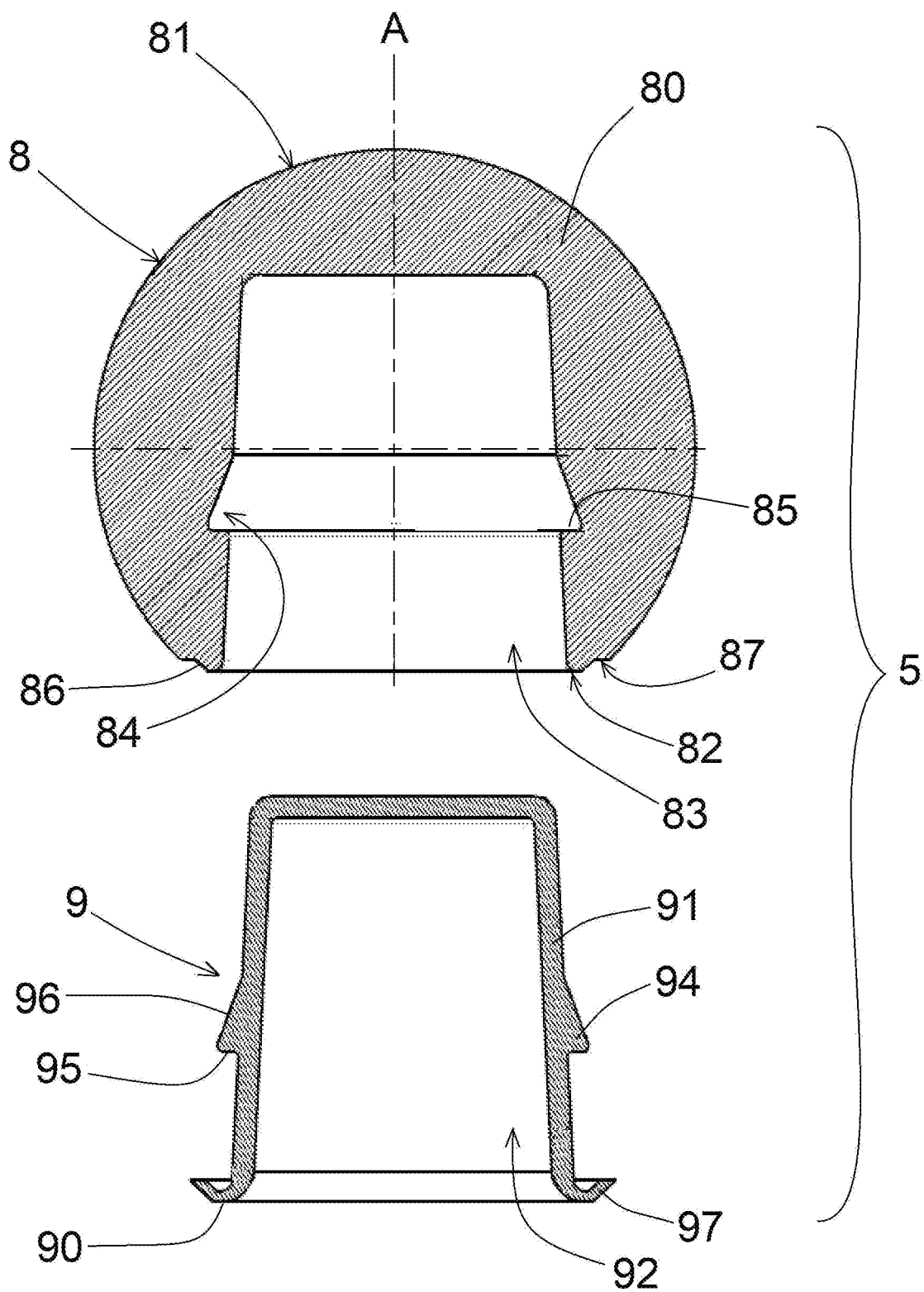
FIG. 20 is an exploded axial view of a variant of the hip prosthesis head of FIG. 6.
Figure 21:
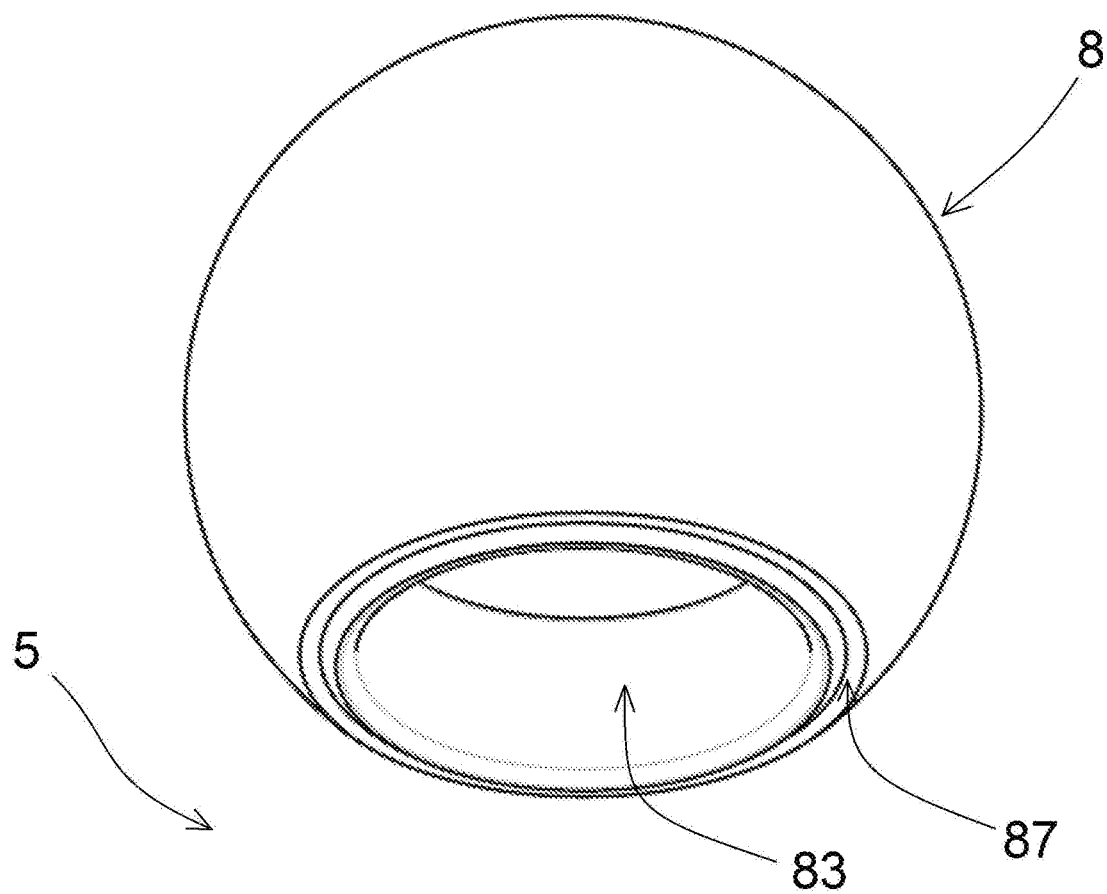
FIG. 21 is an exploded perspective view of the head of FIG. 20.
Figure 21:
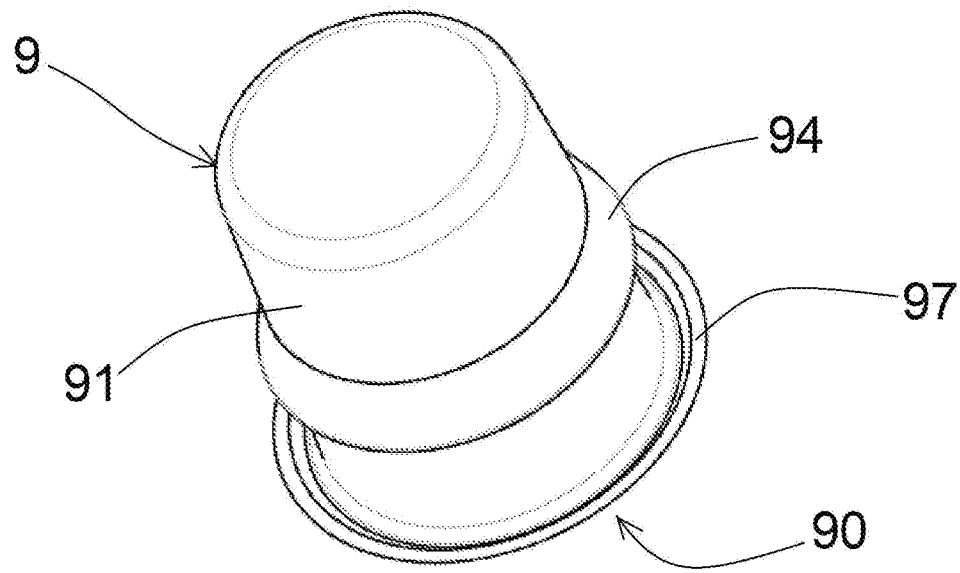

FIGS. 20 and 21 show a variant of the first embodiment of the head (5), wherein an annular groove (87) is defined in the base (90) of the external element in order to receive the annular rib (97) of the base of the internal element, in such a way to center and fix the internal element inside the external element.

Figure 22:
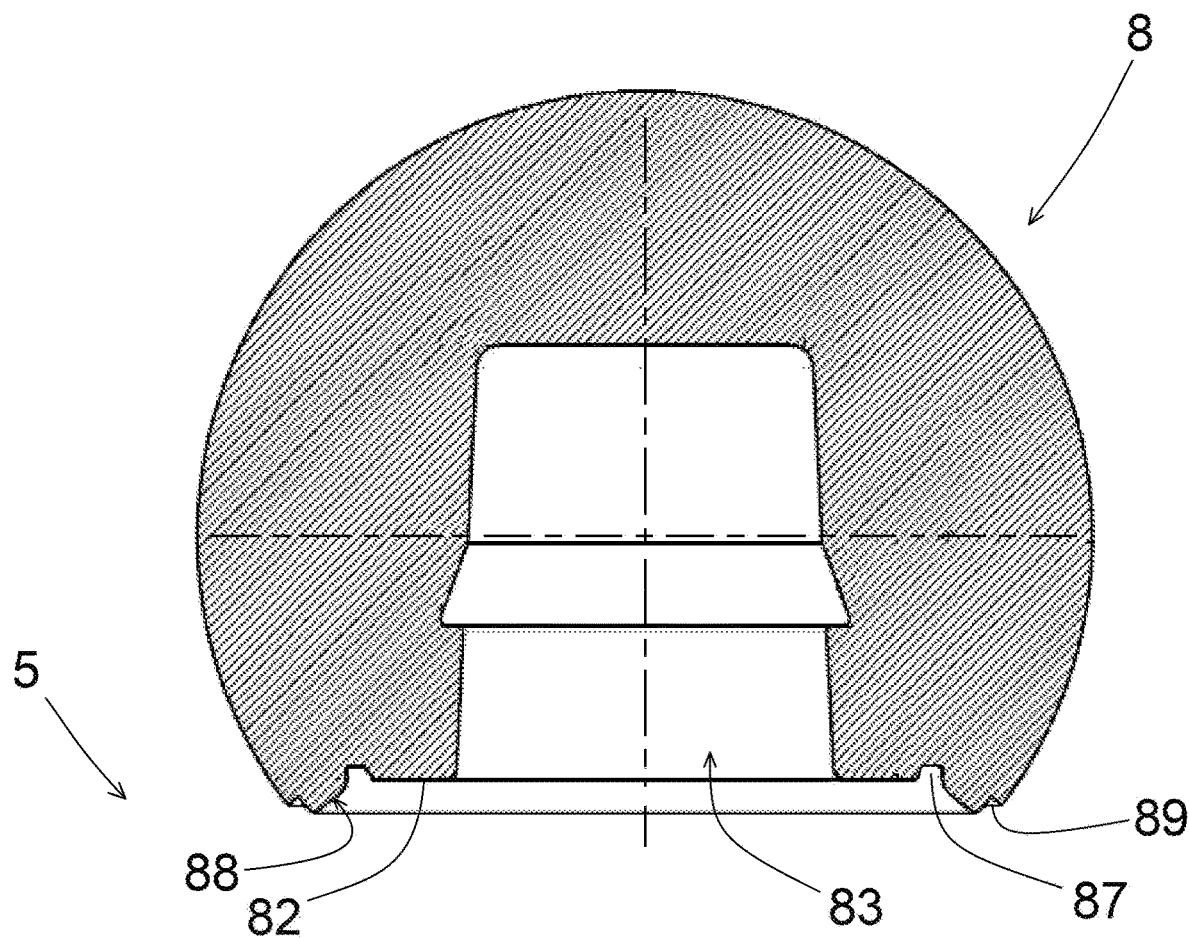
FIG. 22 is an exploded axial view of a variant of the head of FIG. 20.
Figure 22:
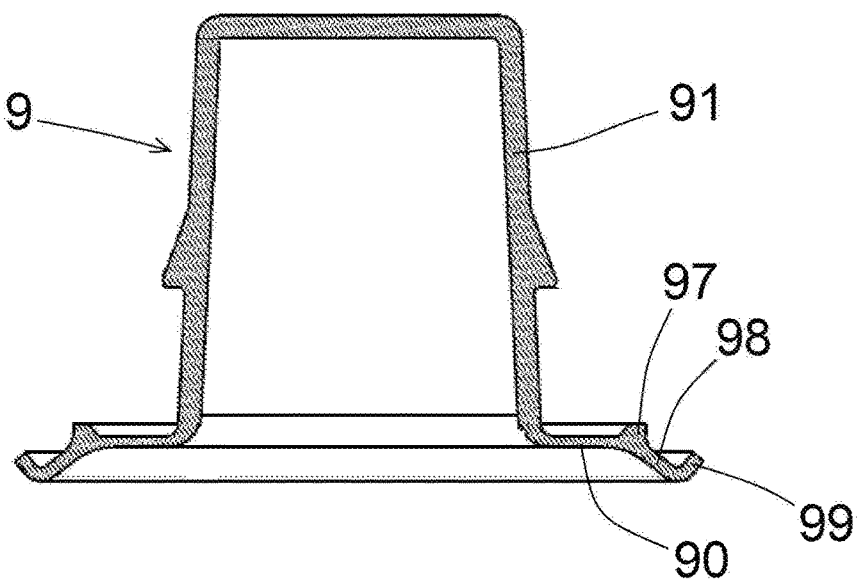
Figure 23:
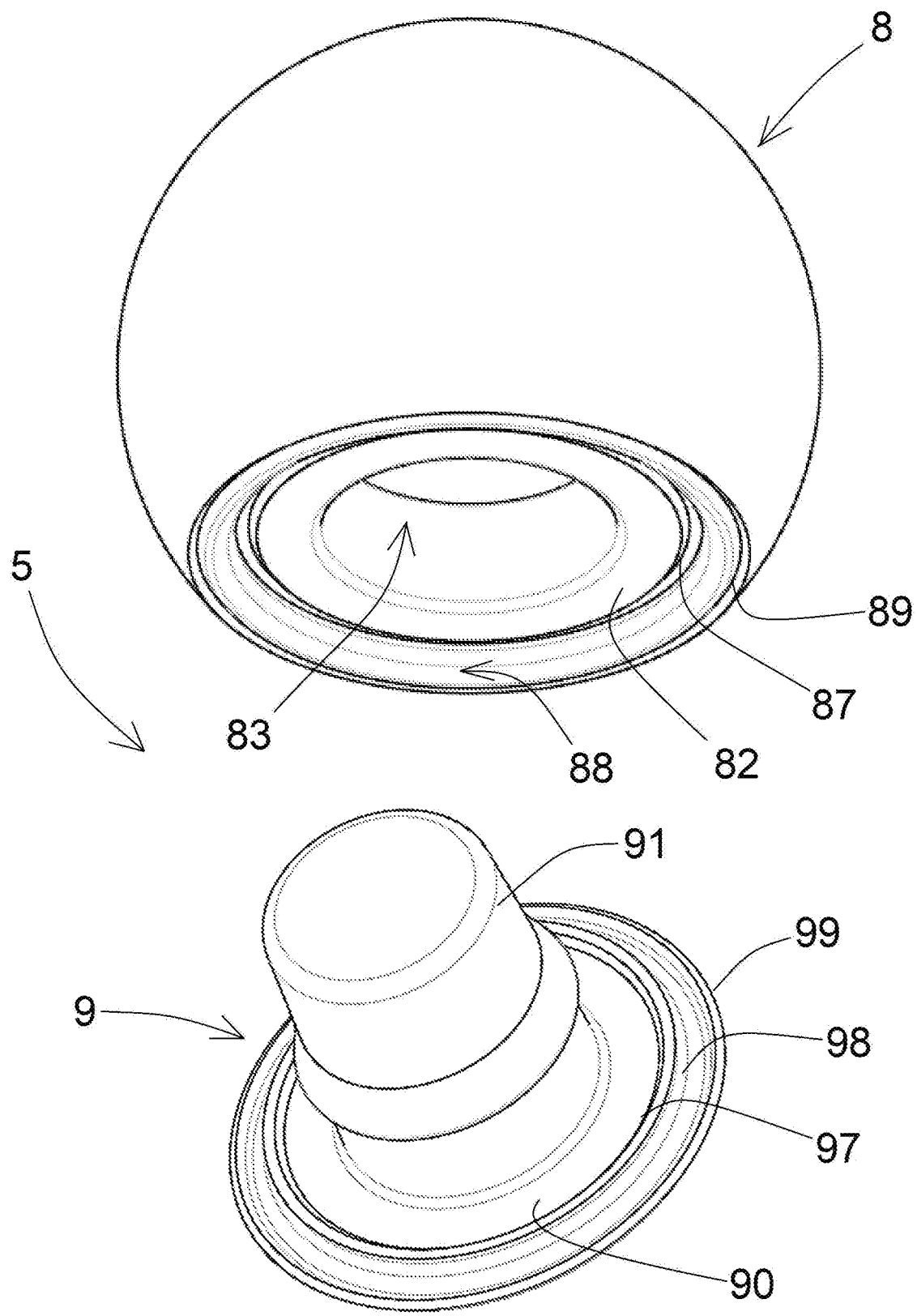
FIG. 23 is an exploded perspective view of the head of FIG. 22.

FIGS. 22 and 23 show a variant of the head (5) of FIG. 20, wherein the base (82) of the external element is disposed in a recessed seat (88) with truncated-conical shape that extends outwards from the annular groove (87) of the base. The recessed seat (88) has a second annular groove (89) with higher diameter than the annular groove (87) of the base.

A tapered wall (98) extends outwards and downwards from the base (90) of the internal element, in peripheral position relative to the annular rib (76) of the base. The tapered wall (98) is suitable for being received in the recessed seat (88). The tapered wall (98) has a second annular rib (99) that extends outwards and upwards and is engaged in the second annular groove (89) of the recessed seat (88) of the external element.

Figure 24:
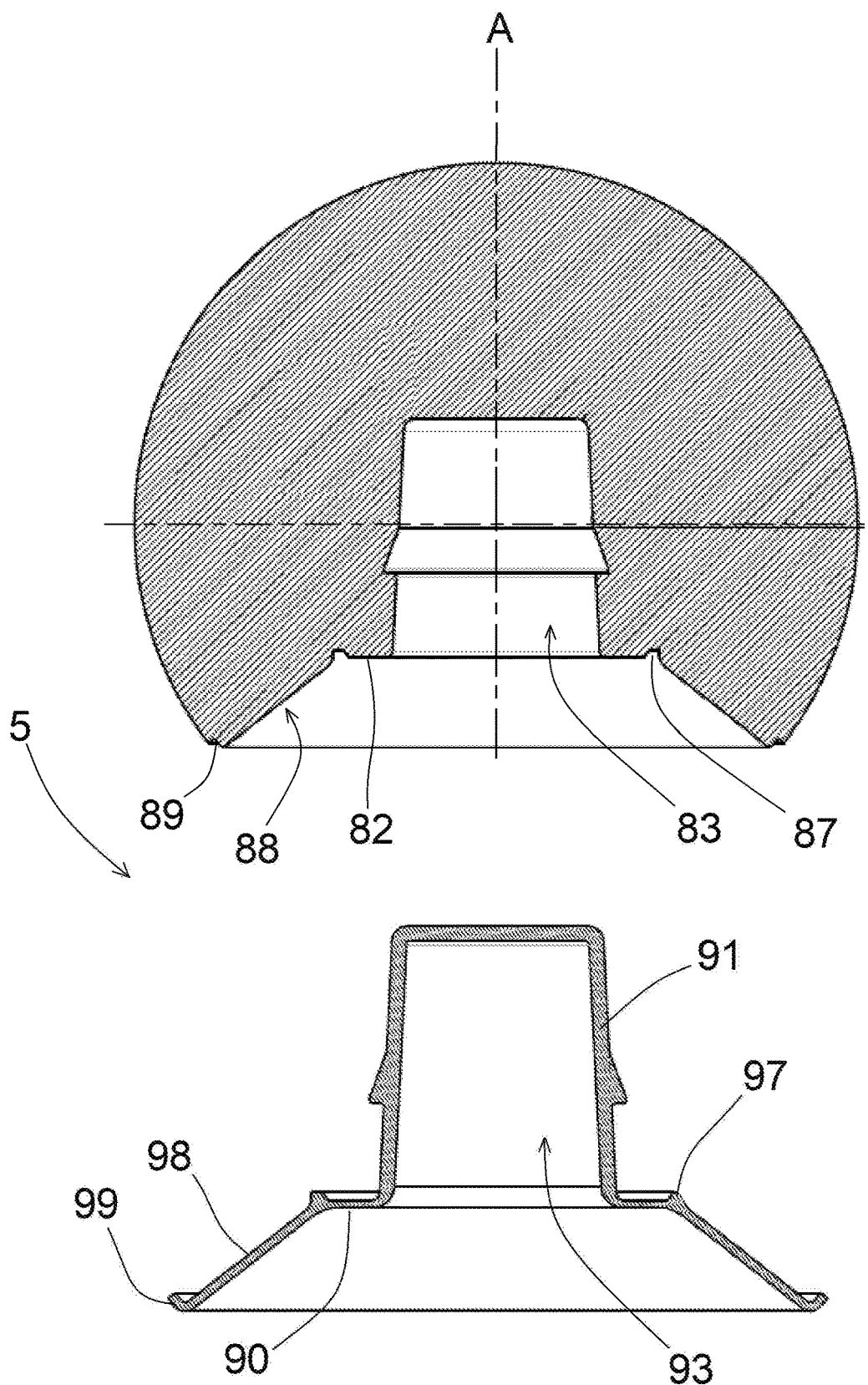
FIG. 24 is an exploded axial view of a variant of the head of FIG. 22.
Figure 25:
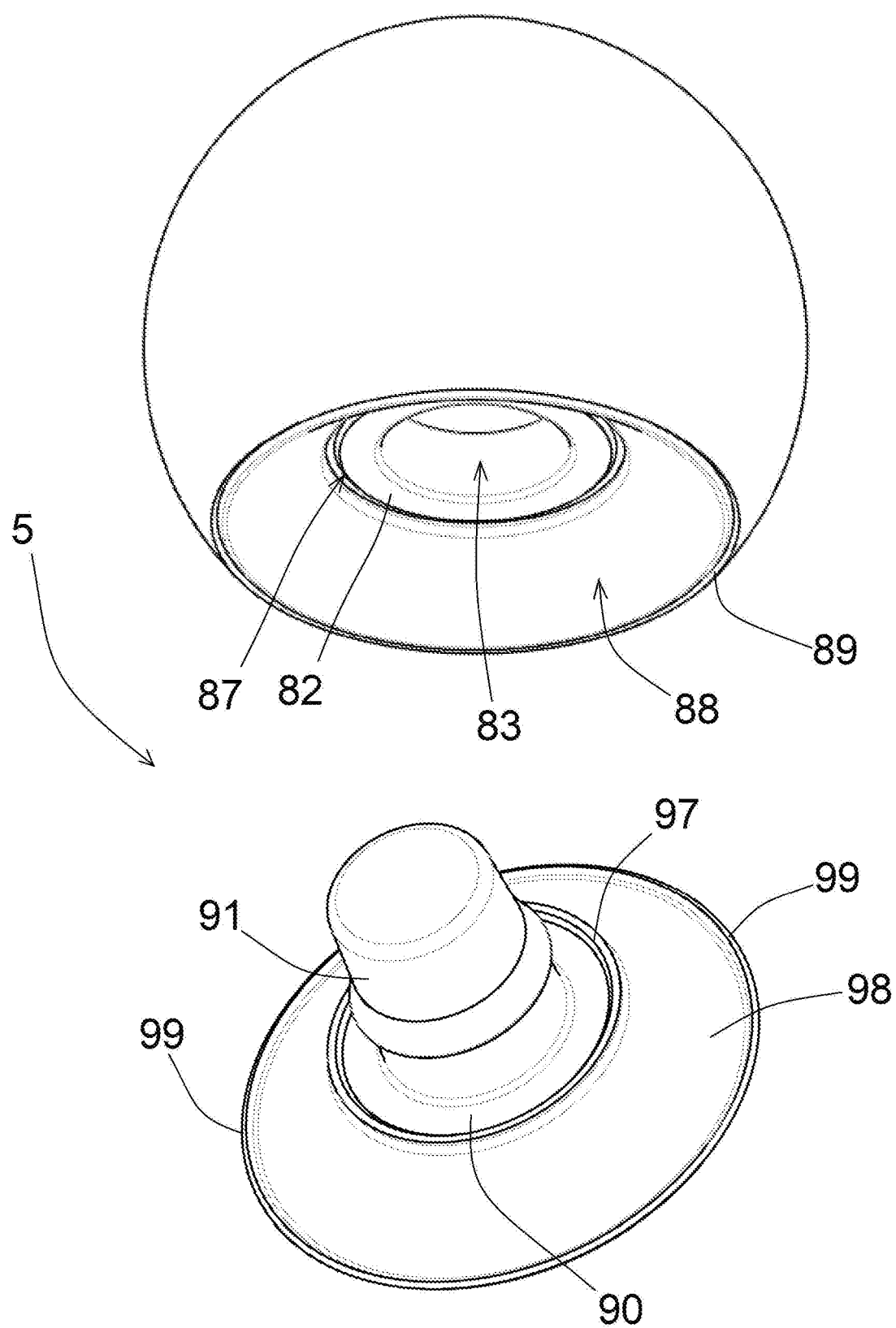
FIG. 25 is an exploded perspective view of the head of FIG. 24.

FIGS. 24 and 25 show a variant of the head (5) of FIG. 22, wherein the recessed seat (88) of the external element and the tapered wall (98) of the internal element have higher dimensions than the ones of FIG. 22.

In any case, the recessed seat (88) of the external element and the tapered wall (98) of the internal element have a conicity angle of approximately 42-62°, preferably 52°, with respect to the axis (A) of the blind hole (83) of the external element.

Figure 26:
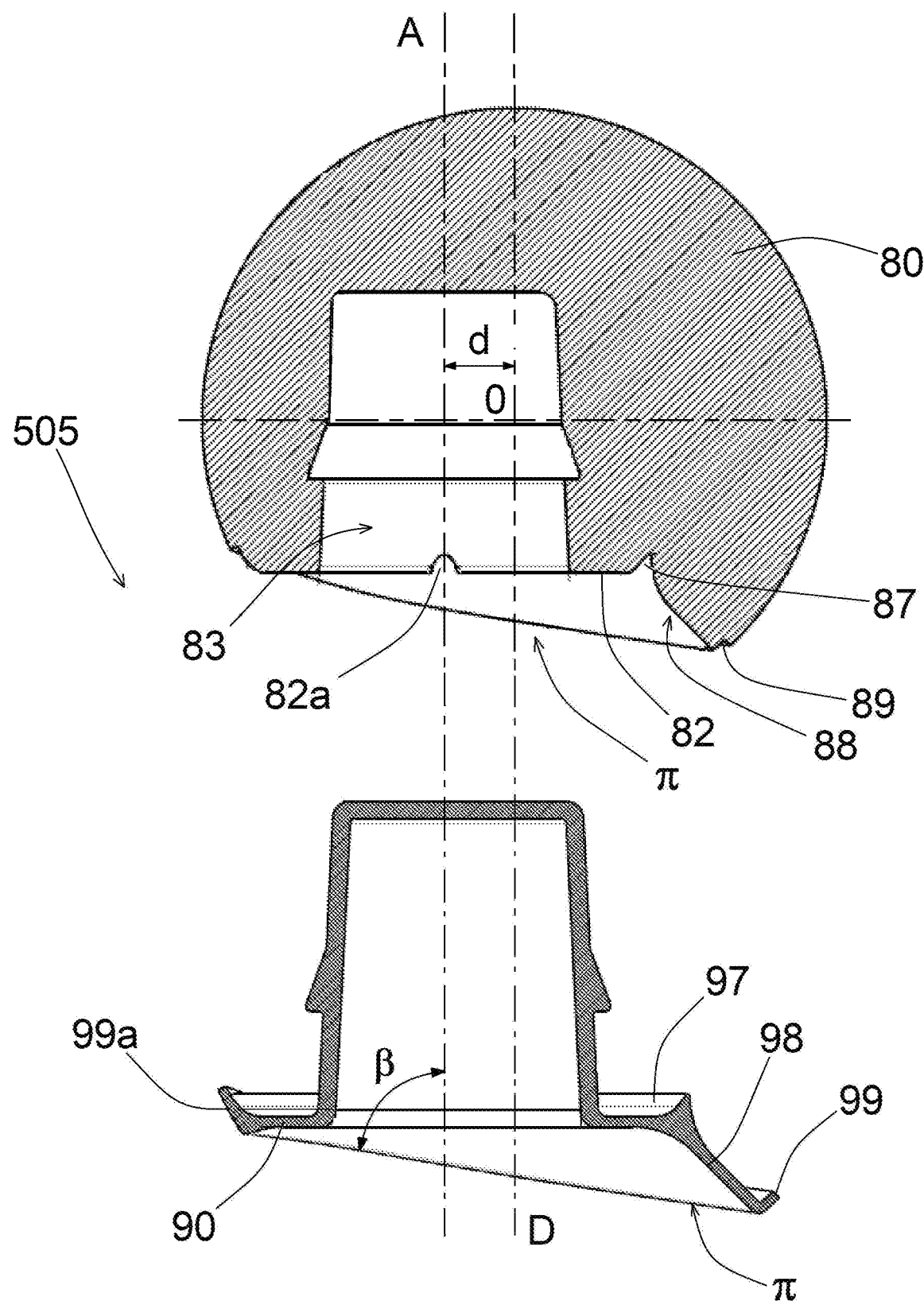
FIG. 26 is an exploded axial view of a hip prosthesis head according to a fifth embodiment of the invention.
Figure 27:
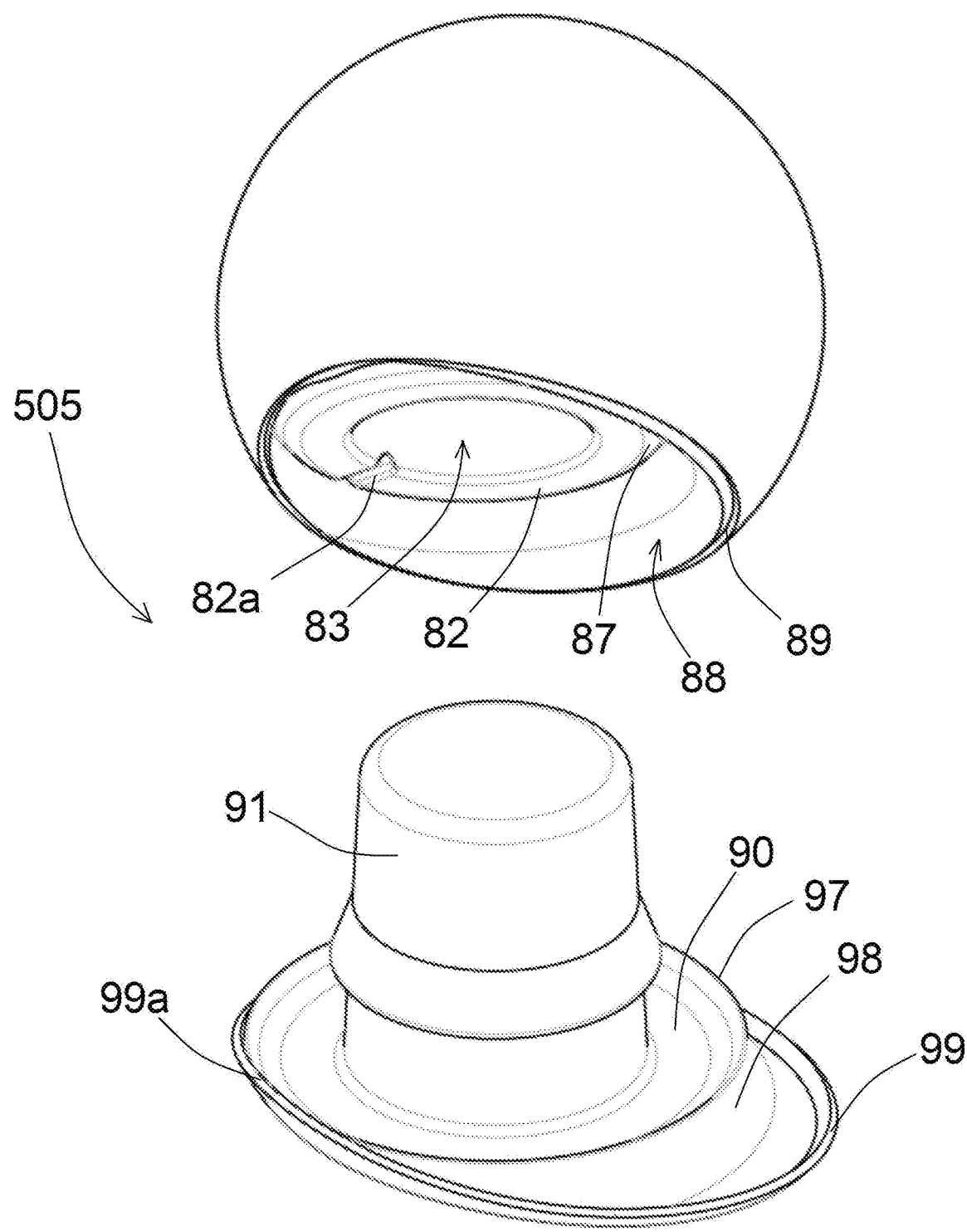
FIG. 27 is an exploded perspective view of the head of FIG. 26.

FIGS. 26 and 27 show a head (505) according to a fourth embodiment, wherein the second annular rib (99) of the tapered wall of the internal element is eccentric with respect to the annular rib (97) of the base (90) of the internal element. Otherwise said, the second annular rib (99) has a center on an axis (D) passing through the center (O) of the body (80) of the external element and the annular rib (97) has a center on the axis (A) of the blind hole (3) of the external element. Therefore, the axis (A) of the blind hole (3) of the external element is spaced from the center (O) of the body of the external element by a distance (d) equal to approximately 4-8 mm.

The recessed seat (88) of the external element and the tapered wall (98) of the internal element are cut by an inclined plane ($\pi$) not orthogonal to the axis (A) of the blind hole (83) of the external element. The inclined plane ($\pi$) is inclined by an angle ($\beta$) of approximately 75°-85° relative to the axis (A) of the blind hole (83) of the external element.

In such an embodiment, a portion (99a) of the second annular rib (99) of the tapered wall of the internal element is tangentially overlapped to the annular rib (97) of the base wall of the internal element.

The base (82) of the external element has a radial groove (82a) that extends from the blind hole (83) to the annular groove (87). The base (90) of the internal element (9) has a radial rib (not shown in the figures) that protrudes in upper position and is engaged in the radial groove (82a) of the base of the external element, in such a way to prevent the internal element from rotating with respect to the external element. Such an arrangement can be provided in any one of the embodiments of the head.

Figure 28:
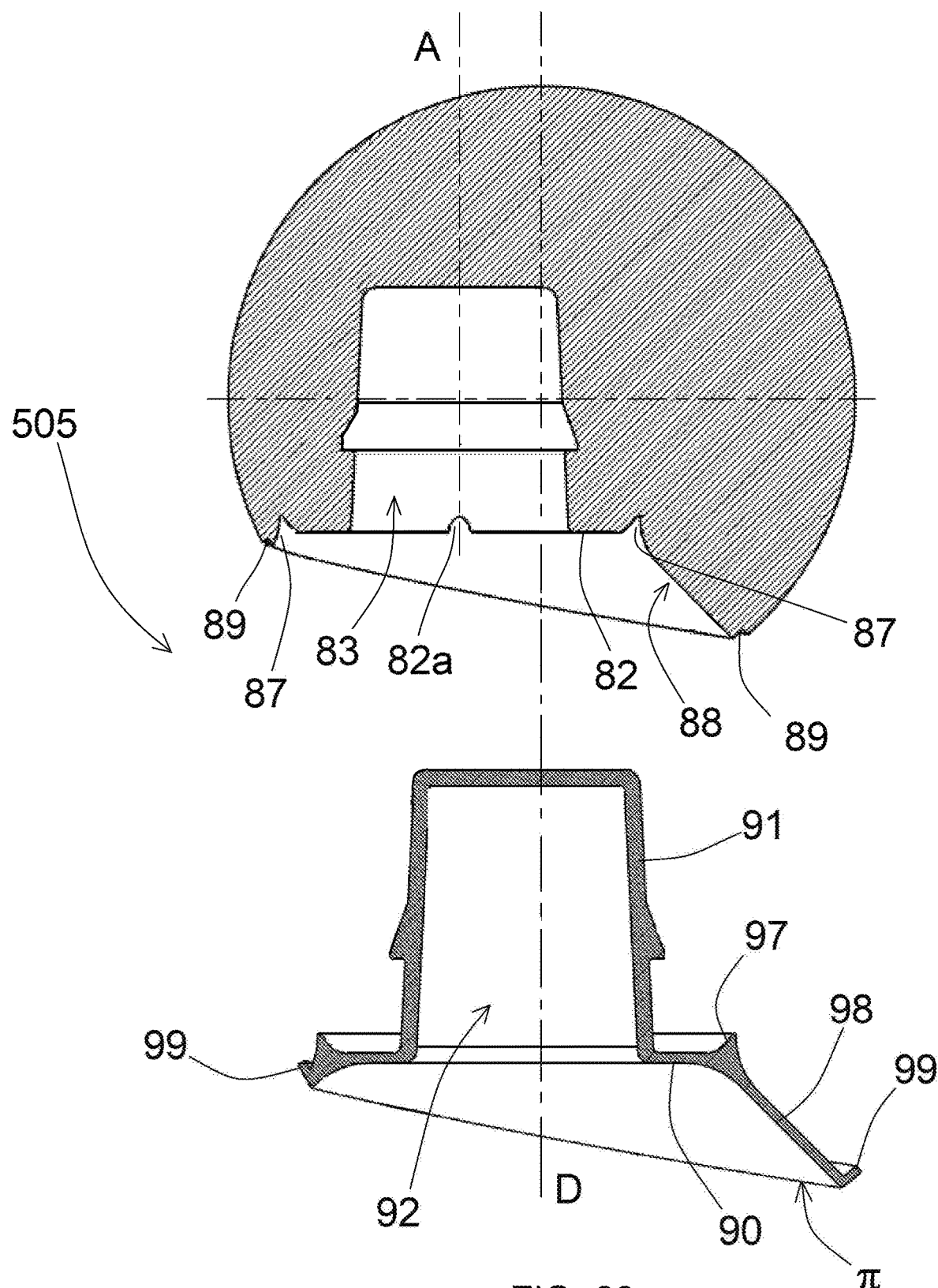
FIG. 28 is an exploded axial view of a variant of the head of FIG. 26.
Figure 29:
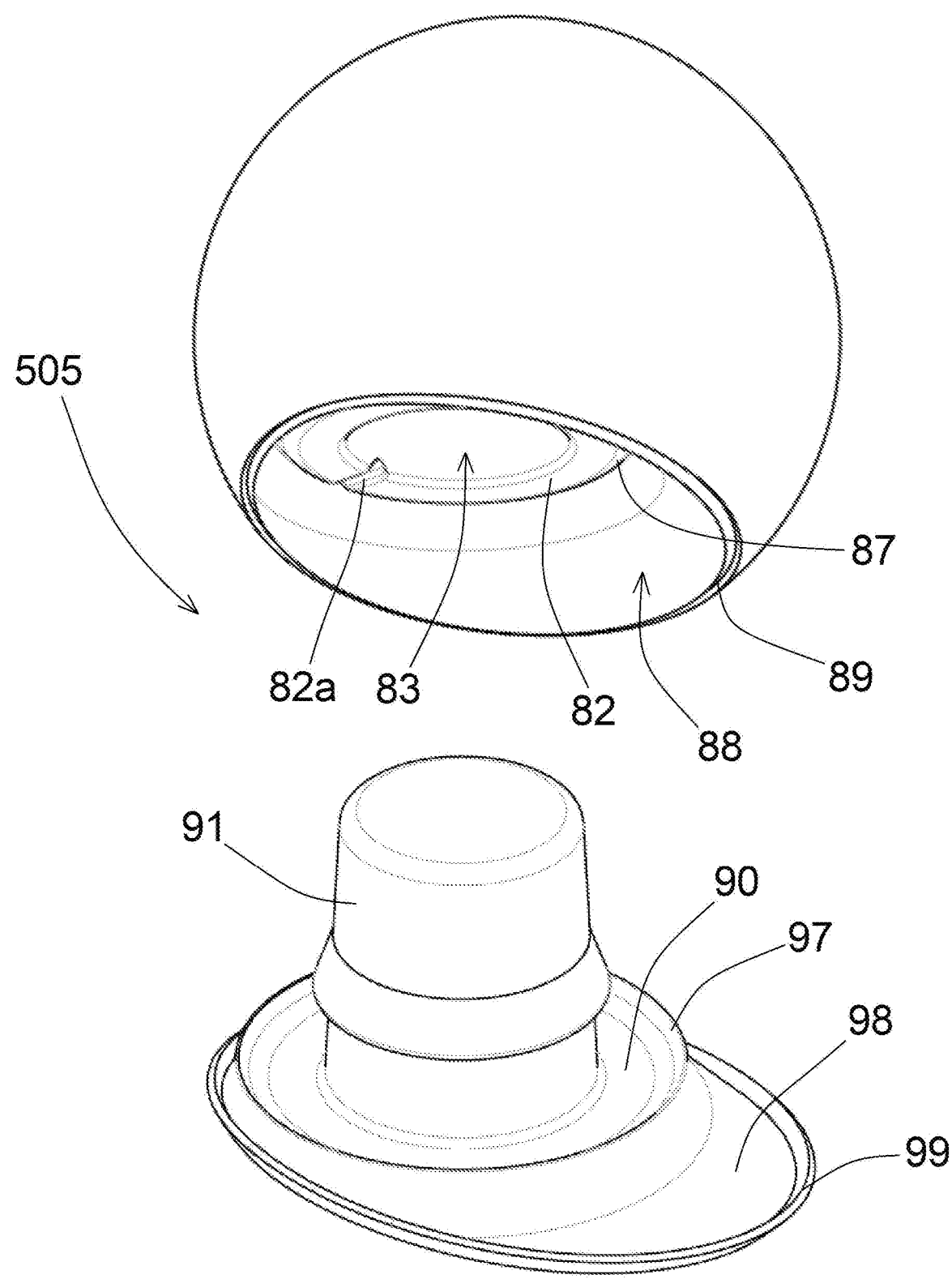
FIG. 29 is an exploded perspective view of the head of FIG. 28.

FIGS. 28 and 29 show a variant of the head (505) of FIG. 26, wherein the second annular rib (99) of the tapered wall of the internal element is always spaced from the annular rib (97) of the base (90) of the internal element.

I claim:

1. A hip prosthesis head comprising:
   an external element having a convex external surface adapted to couple in an omnidirectional coupling mode with a convex internal surface of an acetabular cup so as to be implanted in a pelvic bone or a cotyloid cavity of a patient; and
   an internal element having a truncated-conical seat adapted to couple in a Morse taper coupling mode with truncated-conical shank of a stem implantable in a femur of the patient, wherein said external element and said internal element are formed of different materials, said internal element being coupled inside a blind hole of said external element in a fit-in manner, said external element having an annular base around the blind hole, said internal element having a truncated-conical body that is open at a bottom thereof and an annular base that protrudes radially outwardly from a lower edge of the truncated-conical body so as to contact the annular base of said external element, the annular base of said internal element having a first annular rib of a tapered shape that protrudes outwardly and upwardly from the annular base of said internal element so as to be engaged in a first annular groove of the annular base of said external element, wherein the annular base of said external element is disposed in a recessed seat having a second annular groove in a peripheral portion relative to the first annular groove of the annular base of said external element, the recessed seat having a truncated-conical shape, said internal element having a tapered wall that projects outwardly and downwardly from the annular base of said internal element, said internal element having a second annular rib that protrudes outwardly and upwardly from the tapered wall so as to be engaged in the second annular groove of the recessed seat of said external element.

2. The hip prosthesis head of claim 1, wherein the second annular rib of said internal element is eccentric relative to the first annular rib of the annular base of said internal element, the second annular groove of said external element being eccentric relative to the first annular groove of the annular base of said external element, the blind hole of said external element having an axis spaced from a center of said external element by a distance.

3. The hip prosthesis head of claim 2, wherein the recessed seat of said external element and the tapered wall of said internal element are cut by an inclined plane not orthogonal to the axis of the blind hole of said external element.

4. The hip prosthesis head of claim 1, wherein the annular base of said external element has a radial groove, the annular base of said internal element having a radial rib that protrudes so as to be engaged in the radial groove of the annular base of said external element.

5. The hip prosthesis head of claim 1, wherein the second annular rib of said internal element protrudes externally from the truncated-annular body of said internal element so as to be coupled inside the second annular groove formed in the blind hole of said external element, the second annular rib of said internal element having a collar shape, the second annular groove of said external element having a collar shape.

6. The hip prosthesis head of claim 5, wherein the first rib of said internal element has a radial lower surface and a tapered upper surface, the first annular groove of said external element having a radial lower surface.

7. The hip prosthesis head of claim 1, wherein the truncated-conical seat of said internal element has an axis inclined by an angle relative to a normal axis orthogonal to the annular base of said internal element and passes through a center of curvature of the convex external surface of said external element, wherein the truncated-conical seat of said internal element has an irregular truncated-conical shape.

8. A hip prosthesis head comprising:
   an external element having a convex external surface adapted to couple in an omnidirectional coupling mode with a convex internal surface of an acetabular cup so as to be implanted in a pelvic bone or a cotyloid cavity of a patient; and
   an internal element having a truncated-conical seat adapted to couple in a Morse taper coupling mode with truncated-conical shank of a stem implantable in a femur of the patient, wherein said external element and said internal element are formed of different materials, said internal element being coupled inside a blind hole of said external element in a fit-in manner, said external element having an annular base around the blind hole, said internal element having a truncated-conical body that is open at a bottom thereof and an annular base that protrudes radially outwardly from a lower edge of the truncated-conical body so as to contact the annular base of said external element, wherein the convex external surface of said external element comprises:
   a lower portion having a cap portion shape;
   an upper portion having a cap shape; and
   an intermediate portion having a truncated-conical shape, said intermediate portion joining the lower portion to the upper portion, wherein each of said lower portion and said upper portion and said intermediate portion has an elliptical cross-section with a minor axis and a major axis, the major axis having a length of one millimeter to three millimeters longer than a length of the minor axis, said lower portion having a center and a radius of curvature and being cut at a height of a parallel 30° South and a parallel 20° North, said upper portion having a center and a radius of curvature and being cut in an axial section at a height of parallel 20° North, the radius of curvature of said upper portion being less than the radius of curvature of said lower portion, wherein the center of said lower portion and the center of said upper portion lie on a common axis orthogonal to the annular base of said external element, the center of said upper portion being spaced above the center of said lower portion, the radius of curvature of said lower portion being greater than the radius of curvature of said upper portion, wherein said intermediate portion having a height that is approximately eight to ten times less than a height of the radius of curvature of said upper portion.

9. The hip prosthesis head of claim 1, wherein said external element is formed of a plastic material.

10. The hip prosthesis head of claim 9, wherein the plastic material is cross-linked polyethylene.

11. The hip prosthesis head of claim 10, wherein the cross-linked polyethylene is polyether-ether-ketone.

12. The hip prosthesis head of claim 1, wherein said internal element is formed of a metal material.

13. The hip prosthesis head of claim 12, wherein the metal material is a medical steel.

14. The hip prosthesis head of claim 12, wherein the metal material is a cobalt-chrome superalloy.

15. The hip prosthesis head of claim 12, wherein the metal material is titanium.

16. The hip prosthesis head of claim 10, wherein the cross-linked polyethylene is a vitamin E-enriched cross-linked polyethylene.

17. The hip prosthesis head of claim 12, wherein the metal material is coated with nitrided titanium.

\* \* \* \* \*